United States Patent
Cheal et al.

(10) Patent No.: US 7,044,975 B2
(45) Date of Patent: May 16, 2006

(54) JOINT PROSTHESES AND COMPONENTS THEREOF

(75) Inventors: Edward J. Cheal, Duxbury, MA (US); George B Cipolletti, Duxbury, MA (US)

(73) Assignee: Apex Surgical, LLC, Raynham, MA (US)

( * ) Notice: Subject to any disclaimer, the term of this patent is extended or adjusted under 35 U.S.C. 154(b) by 0 days.

(21) Appl. No.: 10/605,322

(22) Filed: Sep. 22, 2003

(65) Prior Publication Data

US 2004/0107001 A1 Jun. 3, 2004

Related U.S. Application Data

(63) Continuation of application No. 09/583,805, filed on May 30, 2000, now Pat. No. 6,702,854.

(60) Provisional application No. 60/136,815, filed on Jun. 1, 1999, provisional application No. 60/168,526, filed on Dec. 2, 1999.

(51) Int. Cl.
*A61F 2/32* (2006.01)
(52) U.S. Cl. ............................. 623/22.42; 623/22.46
(58) Field of Classification Search .. 623/22.42–22.46, 623/22.11, 19.11, 20.33, 20.27, 20.26, 20.15, 623/20.14, 20.32, 20.34, 21.11–21.19
See application file for complete search history.

(56) References Cited

U.S. PATENT DOCUMENTS

| | | | |
|---|---|---|---|
| 3,846,846 A | 11/1974 | Fischer | 3/1 |
| 4,051,559 A | 10/1977 | Pifferi | 3/1.912 |
| 4,212,087 A * | 7/1980 | Mortensen | 623/26 |
| 4,520,511 A | 6/1985 | Gianezio et al. | 3/1.913 |
| 4,608,055 A | 8/1986 | Morrey et al. | 623/23 |
| 4,624,673 A | 11/1986 | Meyer | 623/16 |
| 4,676,797 A | 6/1987 | Anapliotis et al. | 623/18 |
| 4,693,724 A | 9/1987 | Rhenter et al. | 623/23 |
| 4,790,852 A | 12/1988 | Noiles | 623/18 |
| 4,846,839 A | 7/1989 | Noiles | 623/18 |
| 4,851,007 A | 7/1989 | Gray | 623/23 |
| 4,908,032 A | 3/1990 | Keller | 623/18 |
| 4,963,155 A | 10/1990 | Lazzeri et al. | 623/23 |
| 4,995,883 A | 2/1991 | Demane et al. | 623/23 |
| 5,002,578 A * | 3/1991 | Luman | 623/22.42 |
| 5,002,581 A | 3/1991 | Paxson et al. | 623/23 |
| 5,030,234 A | 7/1991 | Pappas et al. | 623/23 |
| 5,035,712 A | 7/1991 | Hoffman | 623/16 |
| 5,035,717 A | 7/1991 | Brooks | 623/18 |
| 5,047,033 A | 9/1991 | Fallin | 606/87 |
| 5,074,879 A | 12/1991 | Pappas et al. | 623/18 |
| 5,080,674 A * | 1/1992 | Jacobs et al. | 623/20.17 |
| 5,080,685 A | 1/1992 | Bolesky et al. | 623/23 |
| 5,108,437 A | 4/1992 | Kenna | 623/16 |
| 5,108,452 A | 4/1992 | Fallin | 623/23 |

(Continued)

FOREIGN PATENT DOCUMENTS

EP  0 433 121 A1  6/1991

(Continued)

OTHER PUBLICATIONS

International Search Report, International Application Ser. No. PCT/US00/15059.

*Primary Examiner*—Alvin J. Stewart
(74) *Attorney, Agent, or Firm*—Scott E. Kamholz; Foley Hoag LLP

(57) ABSTRACT

Modular joint prostheses and components thereof are disclosed. In an embodiment, a joint prosthesis may include a head member, a neck member, and a stem member.

22 Claims, 16 Drawing Sheets

U.S. PATENT DOCUMENTS

| | | | |
|---|---|---|---|
| 5,135,529 A | 8/1992 | Paxson et al. | 606/85 |
| 5,181,928 A | 1/1993 | Bolesky et al. | 623/23 |
| 5,201,882 A | 4/1993 | Paxson | 623/23 |
| 5,286,260 A | 2/1994 | Bolesky et al. | 623/23 |
| 5,342,366 A | 8/1994 | Whiteside et al. | 606/86 |
| 5,370,706 A | 12/1994 | Bolesky et al. | 623/18 |
| 5,405,394 A | 4/1995 | Davidson | 623/18 |
| 5,507,824 A | 4/1996 | Lennox | 623/22 |
| 5,507,830 A | 4/1996 | DeMane et al. | 623/23 |
| 5,549,706 A | 8/1996 | McCarthy | 623/23 |
| 5,601,567 A | 2/1997 | Swajger et al. | 606/102 |
| 5,653,764 A * | 8/1997 | Murphy | 623/23.15 |
| 5,653,765 A * | 8/1997 | McTighe et al. | 623/22.42 |
| 5,658,349 A | 8/1997 | Brooks et al. | 623/23 |
| 5,702,480 A | 12/1997 | Kropf et al. | 623/23 |
| 5,876,459 A | 3/1999 | Powell | 623/18 |
| 5,888,245 A | 3/1999 | Meulink et al. | 623/23.35 |
| 5,906,644 A * | 5/1999 | Powell | 623/20.15 |
| 6,264,699 B1 | 7/2001 | Noiles et al. | 623/23.23 |
| 6,299,648 B1 | 10/2001 | Doubler et al. | 623/23.18 |
| 6,319,286 B1 * | 11/2001 | Fernandez et al. | 623/23.18 |

FOREIGN PATENT DOCUMENTS

| | | |
|---|---|---|
| EP | 0 562 782 A2 | 9/1993 |
| EP | 0 567 349 A1 | 10/1993 |
| EP | 0 592 897 A1 | 4/1994 |
| EP | 0 612 509 A2 | 8/1994 |
| EP | 0 679 375 A1 | 11/1995 |
| WO | WO 93/02641 | 2/1993 |
| WO | WO 96/00539 | 1/1996 |

* cited by examiner

LONG

LONG +5

LONG +10

MEDIUM

MEDIUM +5

MEDIUM +10

SHORT

SHORT +5

SHORT +10

JOINT PROSTHESES AND COMPONENTS THEREOF

CROSS REFERENCE TO RELATED APPLICATIONS

This application is a continuation of U.S. Ser. No. 09/583,805, filed May 30, 2000 now U.S. Pat. No. 6,702,854, which claims benefit of U.S. Provisional Application Ser. No. 60/136,815, filed Jun. 1, 1999, and of U.S. Provisional Application Ser. No. 60/168,526, filed Dec. 2, 1999. All of the above-listed applications are hereby incorporated herein by reference in their entireties.

BACKGROUND OF INVENTION

1. Field of the Invention

The present invention relates generally to systems, kits and methods for joint replacement using multiple components. In one embodiment, the present invention includes as components a head, a neck and a stem.

2. Related Art

Artificial joint prostheses are widely used today, restoring joint mobility to patients affected by a variety of conditions, including congenital, degenerative, iatrogenic and traumatic afflictions of the joints. The satisfactory performance of these devices can be affected not only by the design of the component itself, but also by the surgical positioning of the implanted component and the long-term fixation of the device. Improper placement or positioning of the device can adversely affect the goal of satisfactorily restoring the clinical bio-mechanics of the joint as well as impairing adequate fixation of the component when implanted within the medullary canal of the bone. The primary role of an implantable joint prosthesis is to restore the extremity distal to the diseased and/or damaged joint to normal function.

As one example, an implantable joint prosthesis can be used to provide an artificial hip. When the prosthesis is situated in this position, significant forces such as axial, bending, and rotational forces are imparted to the device. The prosthesis must endure these forces while remaining adequately fixed within the medullary canal, because adequate fixation is necessary to ensure the implant's proper functioning and a long useful life. Early designs of artificial hip components relied primarily on cemented fixation. These cements, such as polymethylmethacrylate, were used to anchor the component within the medullary canal by acting as a grouting agent between the component and the endosteal (inner) surface of the bone. While this method of fixation by cement provides immediate fixation and resistance to the forces encountered, and allows the surgeon to effectively position the device before the cement sets, it is not without problems. Over time the mechanical properties and the adhesive properties of the bone cement degrade; eventually the forces overcome the cement and cause the components to become loose due to a failure at the cement/bone or cement/stem interface. Alternative approaches to address the issue of cement failure include both biological ingrowth and press-fit stems.

Stems designed for biological ingrowth typically rely on the bone itself to grow into a specially prepared surface of the component, resulting in firmly anchoring the device within the medullary canal. A shortfall of this approach is that, in contrast to components that utilize cement fixation, surfaces designed for biological ingrowth do not provide for immediate fixation of the stem because it takes time for the bone to grow into the specially prepared surface. Press-fit stems precisely engineered to fit within a surgically prepared medullary canal may or may not have specially prepared surfaces and typically rely on an interference fit of some degree of the component within the medullary canal of the bone to achieve stable fixation. Some stem components incorporate sharp cutting flutes or ridges at or near the tip of the stem of the component which are designed to engage in the cortical bone and tend to lock the device in place. A problem with this approach is that once the flutes engage, the rotational alignment of the device is determined.

It is therefore desirable to provide a component which allows adequate rotational alignment and positioning before final placement while achieving sufficient locking for permanent fixation upon full insertion of the device. There is also a need to de-couple the engagement or spacing portion of the stem with the final positioning of the head center, to allow for both optimal positioning and secure engagement to be achieved, independent of each other. The positioning of the device, including the location of the head center relative to the medullary stem portion, effects the biomechanics of the joint. More optimal positioning results in a more efficient joint, and thus lower forces on the device.

By ensuring proper placement of the component one can provide the means for proper functioning and a long useful life of the artificial hip component. Proper placement enables proper function. Placement is typically performed by the surgeon after preparing the medullary canal of the bone to receive the component. Often a surgeon will use a trialing system before implanting the actual component to ensure that the fit and placement is optimized. A trialing system is comprised of trials which are similar in geometry to the actual component and used to assess fit but are intended to be removed, and thus they are usually undersized from the actual component. Alternative methods of trialing to determine predicted fit and proper placement rely on a broaching system. The broaching system is the set of cutting instruments which prepare the medullary canal. Often the broaching systems are designed to perform the trialing function in addition to the bone preparation function by the incorporation of features allowing this dual purpose.

Even though the surgeon goes through extensive preparation to ensure that the ultimate placement of the device will be proper by use of a trialing system, the final placement is dependent on the hand insertion by the surgeon of the implantable component. In cementless components delaying the rotational engagement/alignment of the implantable component before full insertion allows for and can produce more optimal positioning because as the surgeon inserts the device further, optimal placement/position becomes more readily apparent. Additionally, due to the curvature of the femur, the device being inserted tends to follow the curvature as one inserts it, which can cause the device to rotate into a less desirable position. Allowing the surgeon to correct for this rotation before engaging the device fully will also result in more optimal placement. Thus it would be beneficial to have a means for or a device which satisfactorily addresses this issue of obtaining optimal rotational alignment and positioning in a reliable manner.

In cemented components, the problem is somewhat relieved as there is more flexibility in rotational alignment in that final adjustments can be made during insertion before the cement has set. However, it is desirable for movement to be minimized during the cement curing stage as stem movements in the curing cement will almost certainly negatively affect stem-cement attachment. When dealing with cemented components it is important that there be means to allow the stem to remain centrally located within the cement in the medullary canal.

Another problem with prostheses designed for press-fit and/or bone ingrowth fixation is that, in order to achieve adequate stability, the device must make direct contact with cortical bone in the diaphysis, rather than having a layer of intervening bone cement with a lower elastic modulus than that of the stemmed portion of the device. Some components incorporate one or more slots in the distal end of the stem that are designed to increase the stem flexibility, and thus make insertion of the stem easier, and reduce the stresses at the distal tip of the stem in vivo. These slots, however, decrease the strength of the stem relative to a stem with no slot, especially for larger diameter stems that require either a very large single slot or multiple slots to sufficiently reduce the stiffness of the stem. As a consequence, the larger diameter stems are generally more stiff, or weaker, or both, than desirable.

Another consideration related to, but beyond the rotational alignment and positioning of the stem of the device, is that of the resulting head position. The positioning of the device, including the location of the head center relative to the medullary stem portion, affects the biomechanics of the joint. More optimal positioning results in a more efficient joint, and thus lower forces on the device. It is therefore desirable to provide a component that de-couples the engagement or spacing portion of the stem with the final positioning of the head center, to allow for both optimal positioning and secure engagement to be achieved, independent of each other.

The hip head center of rotation is determined by the head position because typical hip heads are spherical. In most devices the head position is determined by the stem position because the two are connected through an integral neck. Many devices in existence use modular hip heads to increase or decrease neck length, which alters both head height and head offset proportionately and simultaneously. The neck portion of the device that is attached to the stem receives the modular heads. This results in the head position being integrally linked and thus aligned with and determined by, the stem portion.

Multiple positions of the heads may be achieved by using hip heads with various bore dimensions and extended or reduced offsets or skirts which limit the positioning of the head to the angled neck axis. In many instances this may not be appropriate as one may only wish to increase offset while maintaining head height (or vice versa), which can not be accomplished with the modular head type devices previously described. In addition, one could not address anteversion of the head in such a device as described. The amount of anteversion is determined by the angular difference between the stem-axis/neck-axis plane to that of the coronal plane. Since the head position is directly linked to the stem position, anteversion can only be achieved by sacrificing stem position by rotating the stem. Thus it would be beneficial to be able to achieve variable positioning of the hip center of rotation independent of stem position as well as independent of both head offset and head height. The ability to de-couple hip head center of rotation from stem positioning would be an additional benefit because it would allow for more freedom in stem placement independent of neck axis placement to achieve the desired anteversion. It is desirable to provide a modular system for joint replacement that provides for this anatomic flexibility.

To conform to a variety of anatomic configurations, devices may incorporate modular components, such as modular stems with modular sleeves, or modular proximal and distal portions of the stem to provide some degree of adjustability for the final stem geometry. This adjustability may or may not include lateral offset, leg length, and/or anteversion, depending on the specifics of the design and on the available components. Such devices have used two basic means of connection, tapers and threads, used alone or in combination. Taper connections have the disadvantage that the final axial position of the two components, relative to each other, is dependent on the precise geometry of the tapers; deviations in geometry within the tolerances allowed for manufacturing results in deviations in the final axial position of the modular component with the tapered connection. The strength of the coupling between the components with the tapered connection is also in part dependent on the level of force used to assemble the components. Similarly, threaded connections have the disadvantage that the strength of connection is in part dependent on the magnitude of torsion applied to the threaded coupling mechanism during assembly. Insufficient impaction force for tapered connections, and/or insufficient torsion for threaded connections, applied during assembly can leave the assembled component at risk of disassembly during the functional lifetime of the device. Unintended disassembly of implanted components is a serious complication that generally requires medical intervention ranging in severity from closed manipulation to surgical revision. This can be a significant risk for tapered and/or threaded coupling means especially considering that the assembly is accomplished in the operating room, rather than under more controlled conditions such as in a factory, in order to take full advantage of the modularity. Thus a design that provides a coupling means for the modular components that has a more reproducible final geometry and reproducible strength of connection, that is less dependent on the surgeon, operating room staff, or other persons acting outside the place of manufacture, would be of significant benefit.

It is furthermore desirable to provide a modular system for joint replacement whose components are easy to assemble in an operating room setting. In certain devices, adjustability is achieved at the expense of simplicity. A complex apparatus with a large number of complicated pieces may require laborious assembly, often while the patient is under general anesthesia. Time spent in selecting and arranging component parts of a complex reconstructive device may add significantly to the patient's anesthesia exposure. In addition, a system with a number of component parts provides for the surgeon a steeper learning curve and a less intuitive feel for the relationship between the implant and the joint being reconstructed. Keeping a modular system simple while still providing valuable anatomic variability would be a significant benefit for doctor and patient alike.

SUMMARY OF INVENTION

Accordingly, it is an object of the invention to provide a component designed to be used either without cement in which the device engages into the cortical bone of the medullary canal to achieve the locking for fixation of the stem, or in a cemented application in which spacing elements are utilized to locate and align the stem portion of the component centrally in the cement mantle within the medullary canal. One embodiment of such a cemented or cementless component allows the surgeon to adjust rotational alignment and positioning of the stem component before full insertion is achieved by placement of the engaging and/or spacing feature.

It is another object of the invention to allow for rotational neck positioning independent of the engagement/positioning of the stem portion of the component after full insertion of the stem portion is achieved. Furthermore, according to the present invention one can accommodate additional novel variable head positioning independently and more extensively than simply increasing or decreasing neck length of the neck portion by utilizing different and distinct neck portions which result in differing ratios of head-offset to head-height when combined with selected modular hip heads. Separate neck portions have the additional benefit of being able to address anteversion of the head position independent of stem placement. The components which comprise these devices are designed such that assembly of the components can be accomplished either before implantation, such as on the back table during surgery, or, alternatively the assembly can be accomplished in a successive fashion, assembling each portion independently during implantation to maximize the benefits of independent positioning of the individual sub-components of the device within the bone.

These and other objects are achieved in one embodiment by the incorporation of flutes or ridges in the mid-shaft portion of the stem which allows substantially more rotational and positional adjustment before final seating of the stem than traditional stems with flutes or ridges at or near the distal tip of the stem. The flutes or ridges in the mid-shaft portion act as the bone engaging feature. The mid shaft flutes or ridges will allow the stem to engage the bone of the medullary canal to ensure a well fixed component while allowing positioning flexibility that does not exist today in devices. The fluted or ridged mid-shaft portion of the stem can also be tapered resulting in a conical geometry of the stem. Adjustment of this taper angle in the mid-shaft portion can achieve increased or decreased rotational and positional adjustment by reducing or increasing the taper angle respectively. Adjustment of the taper angle also can alter the degree of fixation by obtaining greater purchase of bone with an increased taper angle or reduced purchase of bone with a decreased taper angle. In cemented devices the bone engaging portion may be replaced by spacing elements to ensure central positioning and alignment of the device within the cement mantle of the medullary canal.

The stem portions may also incorporate longitudinal slots that increase stem flexibility, and aid in the ease of insertion and of positioning the stem. The number, configuration, and dimensions of the slots are defined so as to provide the appropriate distal stem stiffness while maintaining an adequate strength of the tines. The larger diameter stem portions with slots employ a "V-slot" configuration that provides adequate flexibility, particularly under distal tip loads applied in the posterior-medial direction. The configuration and dimensions of the slots are specified such that the distal flexibility is relatively constant over the range of stem sizes, when the flexibility is normalized to the diameter of the diaphyseal segment of the stem portion.

In one embodiment the neck portion and stem portion may be formed integrally in that they are one piece. In another embodiment, the stem and neck portions are decoupled resulting in two distinct pieces: a modular neck portion which may be combined with a modular stem portion to allow additional rotational alignment and positioning of the neck portion independent from and relative to the stem. This achieves additional variable positioning independent of that achieved after full insertion of the stem portion. The modular neck portion can be locked to the stem portion in one of several positions to achieve the desired amount of rotational alignment. Furthermore the coupling means between the neck portion and the stem portion provides a reproducible strength and geometry of assembly between the two portions; the coupling means only requires some minimum number and force of impaction blows to achieve full assembly, where full assembly is defined by seating of the neck portion to the stem portion. Provided the two portions are fully assembled, the resulting strength of assembly and the axial position of the neck portion relative to the stem portion are dependent on the design and manufacturing tolerances, and are not dependent on the magnitude of force applied during assembly.

By varying neck portion configurations a variety of clinical needs and situations can be addressed such as calcar replacement type devices or satisfying the need of extremely offset necks without requiring a whole new stem system. Many more clinical situations can be addressed by simply using the appropriate neck portion configuration designed for that purpose. The stem portion to which the neck portion attaches can be configured with mid shaft flutes for the cementless stem. Alternatively, the stem portion for the cemented stem can incorporate spacing elements to ensure optimal positioning of the device within the cement mantel within the medullary canal. Additional positioning options exist with either stem portion and the addition of modular heads which are assembled to one of the several neck portions envisioned to achieve independent head offset and head height options. Due to the number of options available, and the desire for a system approach in addressing a multitude of clinical situations with limited components, connection means between the components is simplified and common amongst the components resulting in a reliable, more cost effective, and user friendly means to secure the components either prior to, immediately prior to, or during implantation.

In one embodiment, the system of the present invention may include a stem portion with a proximal end, a midshaft bearing at least one axially directed ridge, and a distal non-ridged shaft. The system may further include a head portion and a neck portion. In one embodiment, the head portion is dimensionally adapted to articulate with a surgically prepared joint socket, and the neck portion is dimensionally adapted for bearing the head portion into an anatomically correct relationship with the surgically prepared joint socket. In one embodiment, the neck portion is formed integrally with the stem portion. In another embodiment, the neck portion is removably attachable to the stem portion and mates therewith. The system may include means for removing the stem portion from the medullary canal of the bone and may include means for detaching the neck portion from the stem portion. The system may further include coupling means for securely attaching the neck portion to the stem portion. In one embodiment, the neck portion may include a male spigot dimensionally adapted for insertion into a female bore. In one embodiment, the male spigot is split distally with at least one axially oriented slot. The male spigot and the female bore may be substantially cylindrical. The male spigot and the female bore may be formed using cylindrical shapes with different diameters. In one embodiment, a preselected circumference of a proximal cylindrical shape is greater than a preselected circumference of a distal cylindrical shape. In one embodiment, the stem portion may include a flat platform that supports the neck portion. The neck portion may include a flat surface that rests upon the stem portion. In one embodiment, the distal non-ridged shaft may be slotted with at least one axially oriented slot. In one embodiment, at least two axially oriented slots are present.

These slots may meet to form an acute angle. In one embodiment, the point of the acute angle is contoured to decrease its acuity.

In one embodiment, the present invention provides for kits that may be used for assembling a joint replacement prosthesis. A kit may include at least four prosthetic members that are selected from a group consisting of stem members, neck members and head members so that at least one stem member, neck member and head member is included in the kit. Each stem member in the kit has a proximal end, a midshaft bearing at least one axially directed ridge, and a distal non-ridged shaft. Each neck member is dimensionally adapted to mate with at least one stem member and has a predetermined size and shape for replacing a segment of joint extending from a long bone shaft to a joint head. Each neck member in the kit is differently size and shaped. The present invention further provides for a kit to assemble a hip prosthesis. This kit may include at least four prosthetic members that are selected from a group consisting of stem members, neck members and head members so that at least one stem member, neck member and head member is included in the kit. Each stem member has a proximal flared end, a midshaft bearing at least one axially directed ridge and a distal non-ridged shaft, and has a predetermined shape for insertion into the medullary cavity of the femur. Each neck member is dimensionally adapted to mate with at least one stem member and has a predetermined size and shape to replace a portion of the femur that includes the femoral neck and the adjacent proximal femur. Each neck member further includes an attachment portion for securement to the upper portion of at least one stem member, and each neck member in the kit is differently size and shaped.

In one embodiment, the present invention provides for an attachment mechanism for securely affixing a stem member of a joint prosthesis to a neck member of a joint prosthesis. The attachment mechanism may include a male spigot and a female bore. According to this attachment mechanism, the male spigot may be seated in the female bore by press-fit so that the seating of the male spigot in the female bore securely affixes the stem member in the neck member in anatomically correct position.

In one embodiment, the present invention provides for a stem component of a joint replacement system that includes a proximal end, a distal end and a shaft. In one embodiment, the distal end is dimensionally adapted for being seated within the medullary cavity of a long bone and is slotted with at least one axially oriented slot. In one embodiment, the present invention provides for a system for seating an implantable joint prosthesis in a surgically prepared bone that includes a stem with a proximal end, a distal end, a midshaft, and a distal shaft. According to this embodiment, the distal end is dimensionally adapted for insertion into a medullary cavity of the bone and a distal end is slotted with at least one axially oriented slot. Furthermore, the midshaft bears at least one axially oriented ridge suitable for cutting into a cortical surface of the medullary cavity. Furthermore, the distal shaft is unridged. In this embodiment, when the stem is seated within the bone, the proximal end extrudes from the proximal part of the surgically prepared bone.

In one embodiment, the present invention provides for implantable modular prosthesis for replacing a hip joint. In one embodiment, the prosthesis includes a stem portion with a proximal flared end, a midshaft bearing a plurality of axially directed flutes, and a distal non-fluted shaft. In one embodiment, the prosthesis further includes a head dimensionally adapted for insertion into a surgically prepared acetabulum. In one embodiment, the prosthesis further includes a neck portion positioned in continuity with the proximal flared end of the stem portion and positioned proximal to the proximal end of the femur; the neck portion is dimensionally adapted for bearing the head into an anatomically correct relationship with the surgically prepared acetabulum and for orienting the surgically prepared femur in an anatomically correct position.

The present invention further provides methods for replacing a joint. In one practice of the present invention, a method includes the steps of providing a stem portion, a head portion and a neck portion, resecting the joint head and preparing the medullary cavity of the bone shaft, identifying a proper position for assembling the stem portion, neck portion and head portion so that their assembly restores a proper anatomic relationship, positioning the stem portion in the medullary cavity, assembling the stem portion, neck portion and head portion, and securing the stem portion, neck portion and head portion in their preselected positions. In another practice of the invention, the following steps may be included: providing a modular joint replacement system that includes at least one stem, neck and head, selecting a stem, neck and head, positioning the stem in a medullary cavity of a bone shaft, identifying a proper position for assembling the stem, neck and head so that their assembly restores a proper anatomic relationship, assembling the stem, neck and head in the proper position, and securing the stem, neck and head in the proper position. In another practice of the invention, methods may be provided for replacing a hip joint. According to one practice of this method, steps may include providing a stem portion, a neck portion and a head portion, resecting the joint head and preparing the medullary cavity of the femur, identifying a proper position for assembling the stem portion, neck portion and head portion, positioning the stem portion in the medullary cavity, assembling the stem portion, neck portion and head portion in position to restore a proper anatomic relationship to the hip joint, and securing the stem portion neck portion and head portion in appropriate positions.

BRIEF DESCRIPTION OF DRAWINGS

Features and advantages of the present invention will become apparent to one of ordinary skill in the art by reference to the following drawings, taken in conjunction with the detailed description thereof, with the reference numerals given in the text corresponding to similarly numbered structures in the drawings, and with like numerals referencing like features throughout, wherein.

DETAILED DESCRIPTION

Figures 1A, 1B:
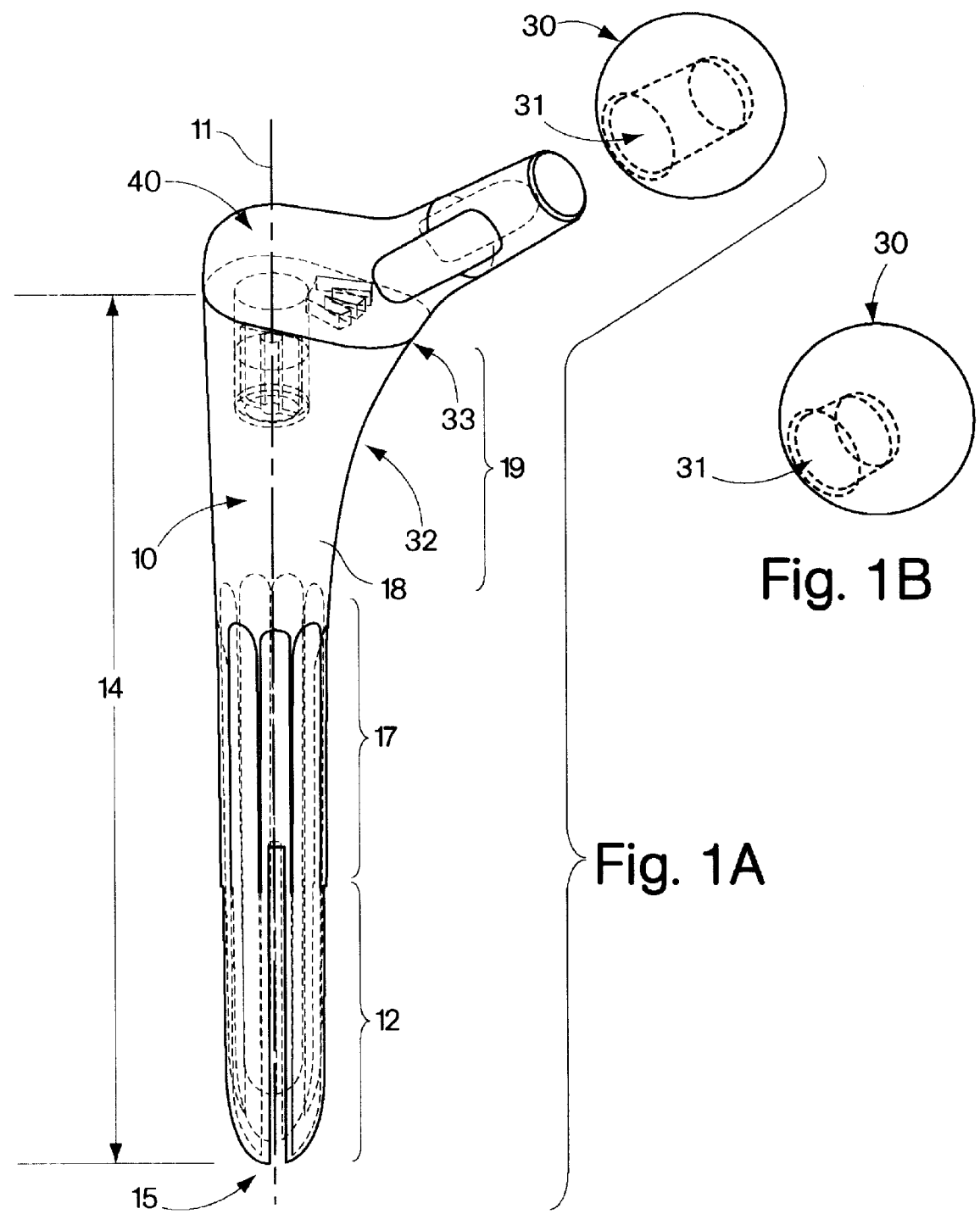
FIG. 1A is a transparent partially exploded view of a prosthetic device according to the present invention.
FIG. 1B depicts an embodiment of a modular hip head.

The present invention is suitable for replacement of any joint comprising a bone shaft, a joint head bearing articular cartilage and in anatomic continuity with the bone shaft, and a joint socket bearing articular cartilage that receives the joint head and permits motion of the joint head and the bone shaft relative to the joint socket. Examples of joints where a single rounded joint head may be found articulating with a cupped joint socket include the hip, the glenoid, the metacarpophalangeal joints and the metatarsophalangeal joints. The present invention is well adapted for prosthetic replacement of these joints. The systems, kits and methods of the present invention may also be adapted for use in joints wherein the joint head comprises two condyles, as in the knee or the interphalangeal joints, or in joints such as the radial elbow joint where a single humeral condyle acts as a joint head articulating with a joint socket on the radial head. In providing a prosthesis according to the present invention for any one of these joints, the system may include a stem portion for insertion into a surgically prepared medullary cavity of a long bone and a neck portion integral with or mated to the stem portion that bears a head portion which articulates with a surgically prepared joint socket. A system according to the present invention is adapted for restoring functional joint and distal extremity mobility at a particular joint by replacing the anatomic joint with a prosthetic joint. The instant invention may achieve this restoration of function by providing a prosthesis that bears a prosthetic head into an anatomically correct relationship with a surgically prepared joint socket. The term "anatomically correct relationship," as used herein, includes those structural arrangements in which the dimensional and anatomic relationship of the prosthetic components either replicates an individual patient's normal anatomy or positions the components of the joint replacement system and their bony anchorages so as to optimize distal extremity or joint function. As will be understood by practitioners in the art, restoring the normal anatomic relationships related to a joint is often the most satisfactory way to optimize distal extremity or joint function. However, in certain situations, a physician will determine that a modification of the normal anatomic relationships might be more suitable for a particular patient due, for example, to other joint or extremity malformations or malpositions. In these cases, the physician may be able to make measurements or perform calculations that will yield dimensions and positions for the joint components that will reconstruct the joint with a modified anatomy that deviates from the normal anatomic configuration but nonetheless is functionally preferable. These anatomic modifications fall within the scope of the term "anatomically correct relationship," as the term is used herein.

The present invention is particularly advantageous in allowing optimal placement and secure attachment for use in an artificial hip and as such this description will reference a hip prosthesis for illustrative purposes.

Figure 2:
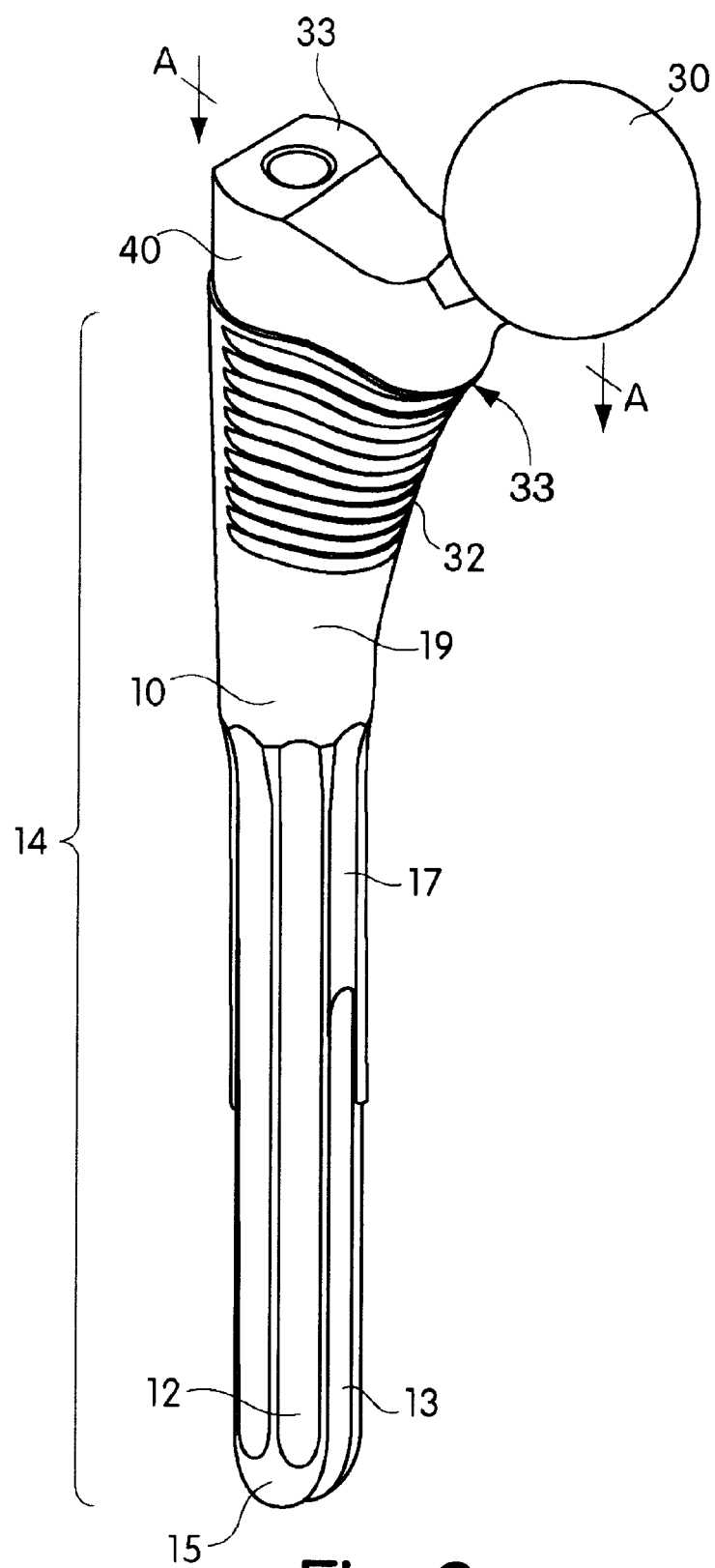
FIG. 2 is a perspective view of another embodiment of a prosthesis according to the present invention.
Figure 3A:
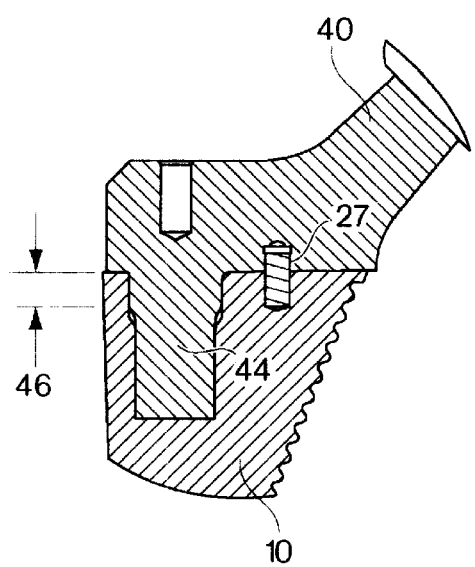
FIG. 3A is a longitudinal cross-section taken along the line of FIG. 3B.
Figure 4:
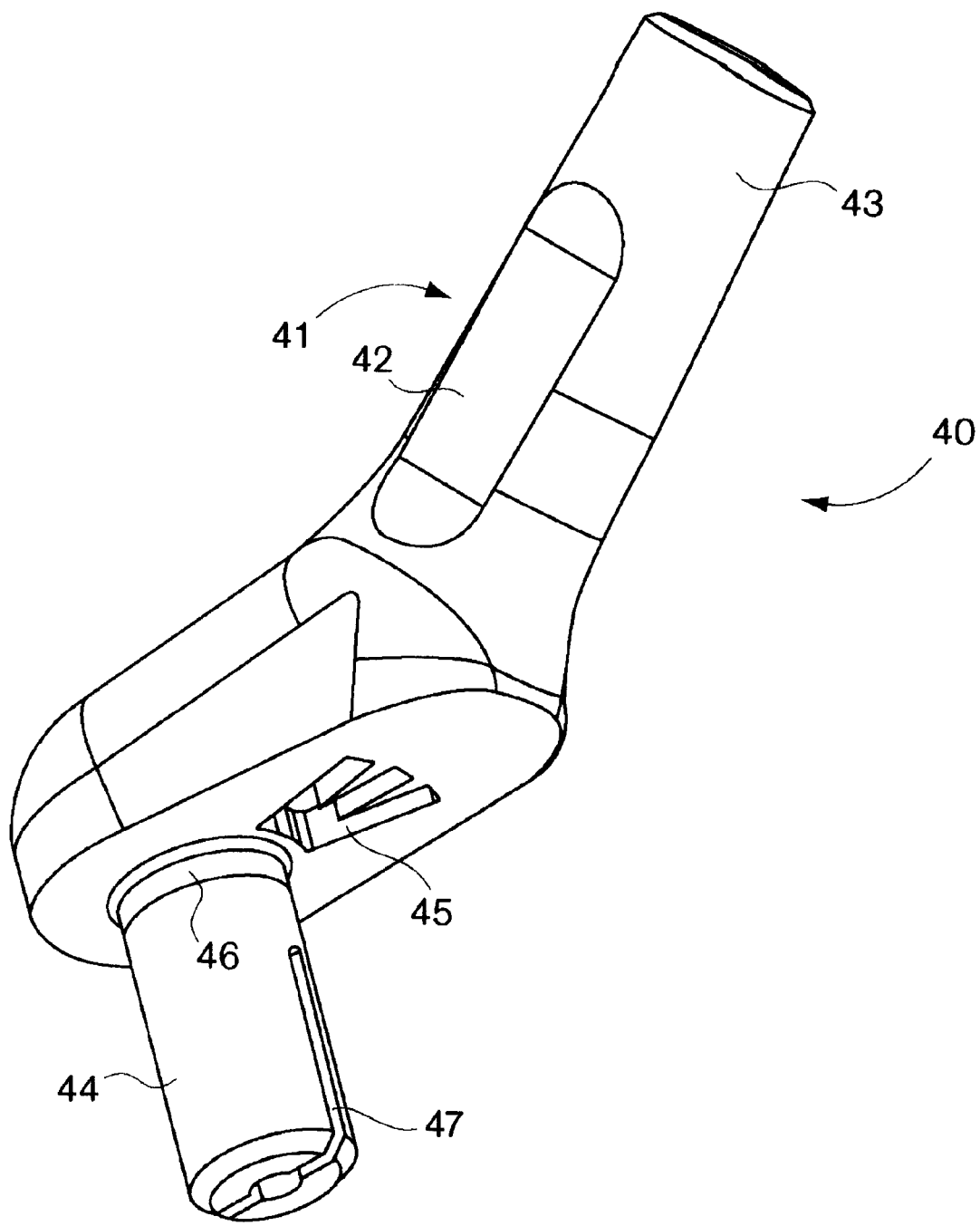
FIG. 4 is a perspective view of the modular neck portion and locking/positioning geometry of an embodiment of the present invention.
Figure 13:
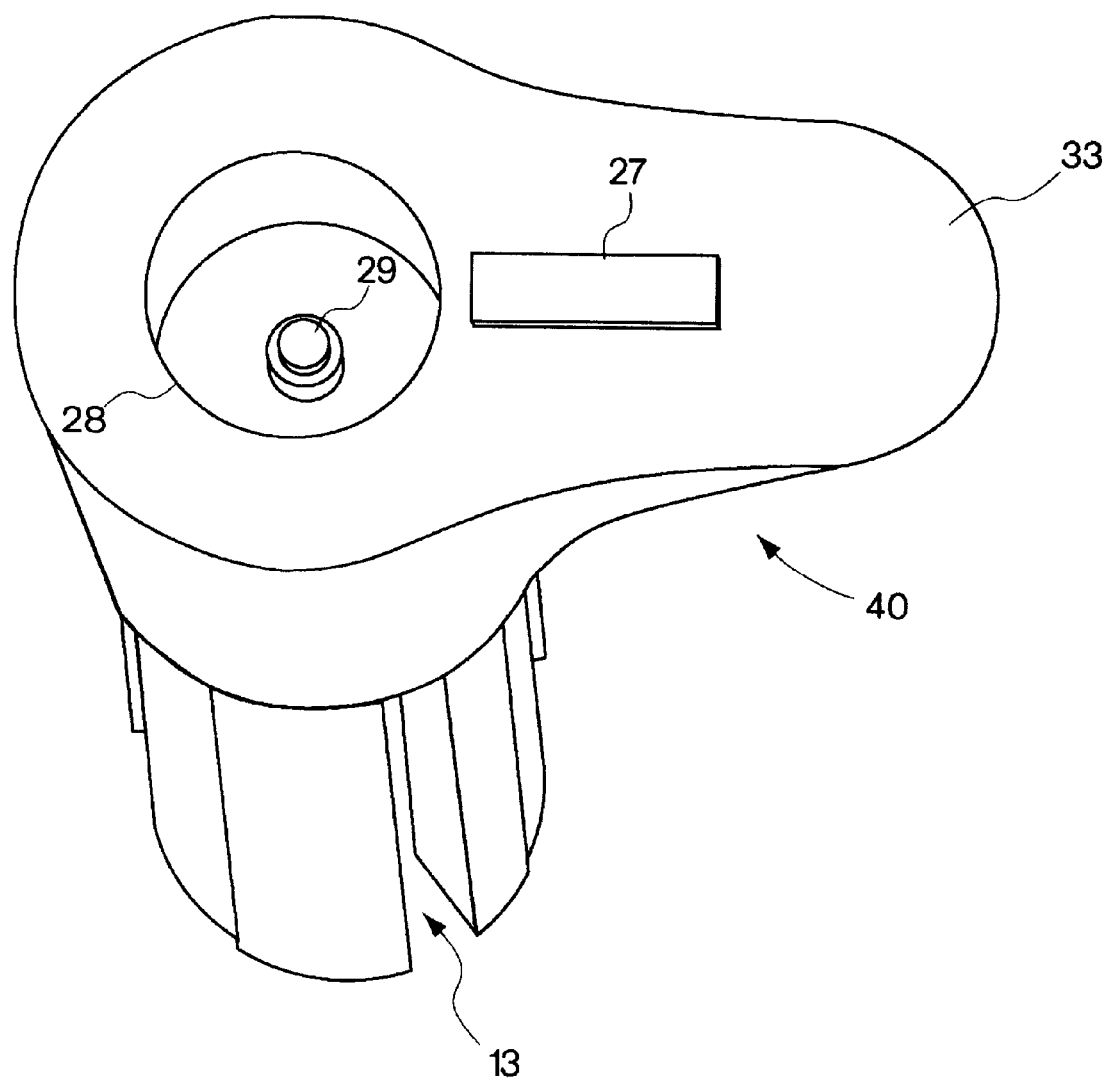
FIG. 13 is a perspective view showing the proximal aspect of a stem according to the present invention.

As shown in FIGS. 1A, 1B, and 2, a prosthesis according to the present invention includes an elongated stem portion (10) of the device which is the portion that is inserted into the medullary canal of the bone. The device also includes a neck portion (40) which may be integral with the stem portion (10), as shown in FIG. 2. In the embodiment depicted in FIG. 1A, the stem portion (10) is independent from the neck portion (40), the two portions being assembled and joined by a locking means, an example of which is shown in FIGS. 3A, 4 and 13. To complete the prosthesis, a modular hip head (30) can be attached to the neck of the one-piece integral stem and neck component or to the non-integral neck (40) which has means for attachment to the stem portion (10). The assembly of the device is not limited temporally, in that assembly can occur before surgery, immediately prior to implantation, or during implantation. The attachment means described below allows for ease of assembly even when access is limited by the surgical exposure.

FIG. 3A shows an embodiment of an attachment mechanism for attaching the neck portion (40) to the stem portion (10). The attachment mechanism comprises both means for coupling the two parts together and means for locking them securely together in an anatomically correct relationship. The end of the neck closest to the stem may be called the attaching end of the neck, and the end of the stem closest to the neck may be called the attachment end of the stem. The end of the neck closest to the joint socket may be called the articulation end and the end of the stem that is inserted in the bone may be called the insertion end. In these figures, the neck (40) bears a male spigot (44) that may be inserted into a central bore (28) within the stem (10). The spigot (44) and the bore (28), may be substantially cylindrical, or may incorporate a proximal locking band (46) as illustrated and as described in more detail below. A key or tab (27) is provided on the top proximal flat (33) of the stem (10) to secure a particular rotational alignment of the neck with respect to the stem. FIG. 4 depicts a receiving slot (45) on the neck into which the key or tab (27) from the stem may be inserted. In an alternate embodiment, not illustrated, a set of longitudinal ridges or longitudinal grooves may be arranged circumferentially within the central cylindrical bore of the stem, designed to mate with matching grooves or ridges arranged with similar spacing along the male spigot of the neck. Matching together a set of grooves and ridges by rotating the neck to a preselected angle with respect to the coronal plane of the patient would permit different anteversion angles to be set and secured while providing resistance to torsional stress and eliminating the need for an alignment pin. These grooves and ridges may be deployed along a vertical section of the bore and the spigot or may extend along the entire vertical height of each structure. With this ridges and grooves arrangement, at least some portion of the stem/neck engagement would resemble a gear with teeth adapted for fitting into notches, but unlike a gear mechanism, the teeth of the gear would be precisely machined to permit a press fit of the neck onto the stem. While the depicted embodiments show the male spigot as part of the neck and the female bore as part of the stem, it is understood that the spigot could be borne on the stem and the bore could be borne on the neck in other embodiments intended for particular anatomic areas. Further, while the depicted embodiments show a receiving slot on the neck with a key or tab on the stem, the positions of these elements could be reversed without departing from the scope of the disclosed invention.

FIG. 4 also shows in more detail a neck portion (40) configured to mate with a stem, as described herein. While this figure shows a coronal split (47) in the male spigot (44), the spigot (44) may also be made solidly, as shown in FIG. 3B.

Figure 3B:
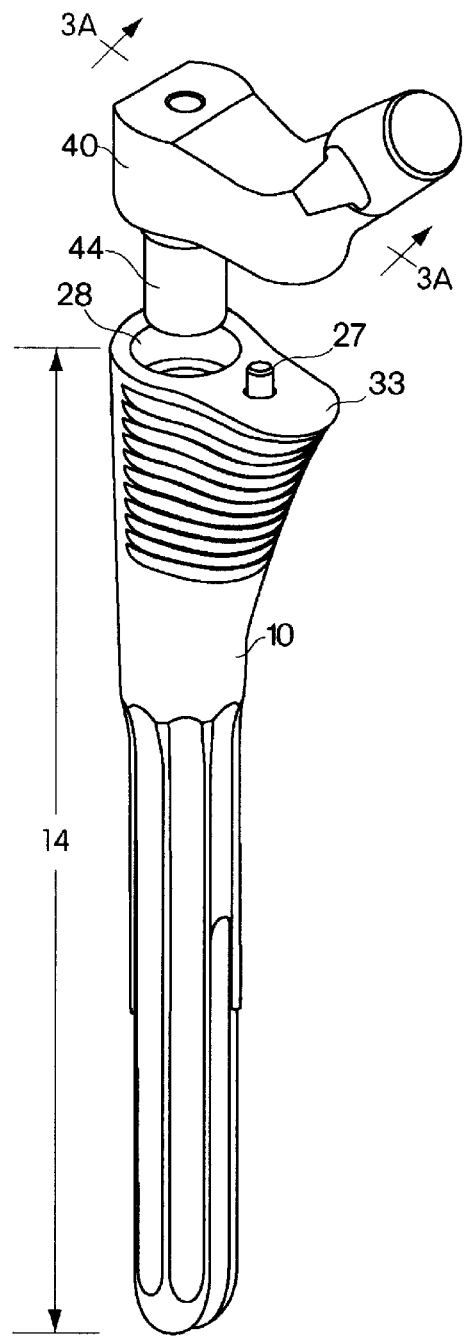
FIG. 3B is a perspective view showing the fit between a stem and a neck.

FIG. 3B further shows that the neck portion (40) can be independent of the stem portion (10) and assembled and joined to the stem portion prior to final implantation. This modular feature is what allows the surgeon additional flexibility in final stem placement beyond that allowed with the features of the fluted mid shaft portion (17) described below. By de-coupling stem placement with head and neck placement, substantially more versatility is allowed and the ability to address anteversion becomes available. The number of positions of the head and neck portion (40) can be quite large, as illustrated representatively in FIG. 6. However, as a matter of manufacturing practicality, the positions may be limited to several discrete positions and still address the positioning need by the surgeon during implantation.

Figure 5:
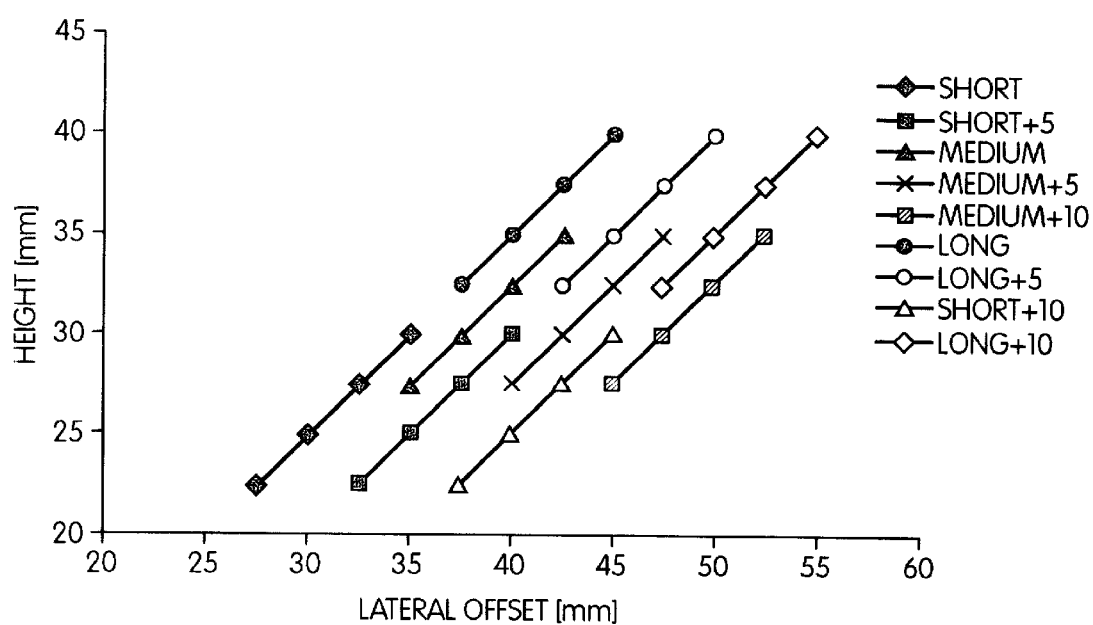
FIG. 5 is a graph showing relations between neck-head locations and lateral offset.
Figure 6A:
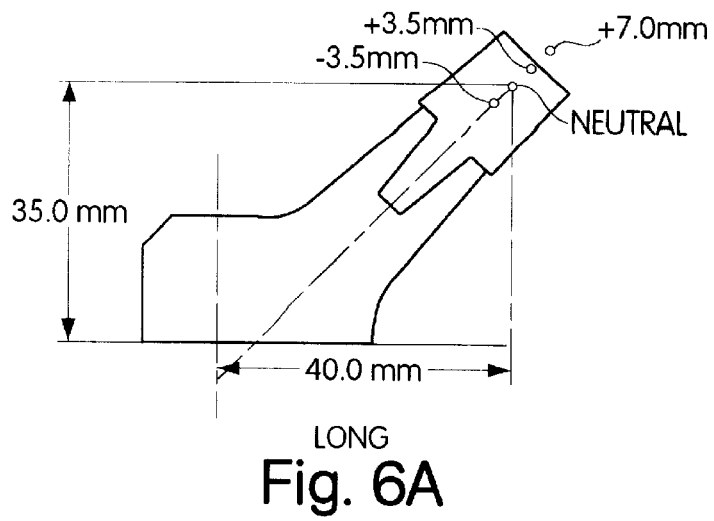
FIG. 6 shows a variety of silhouettes of neck shapes and sizes used to produce the data points shown on FIG. 5.
Figure 6B:
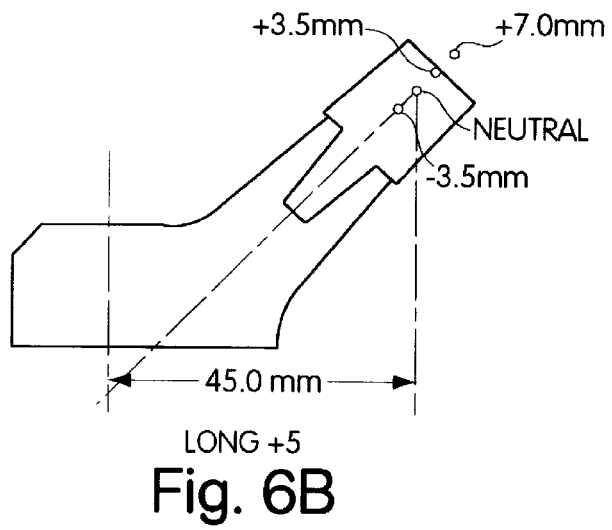
Figure 6C:
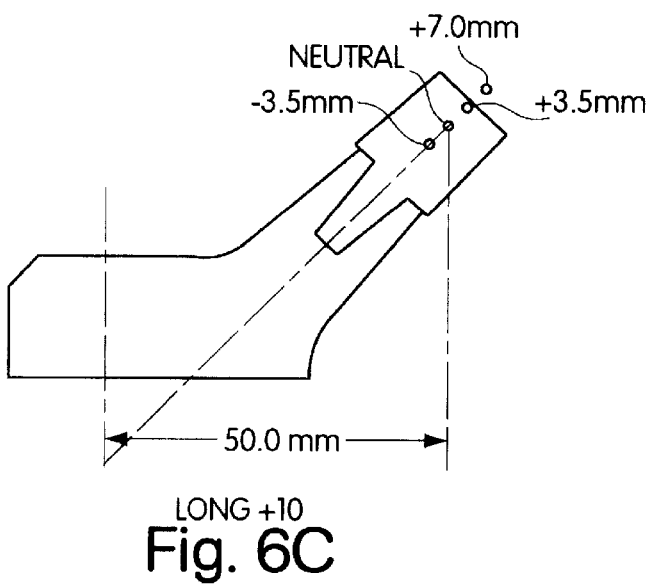
Figure 6D:
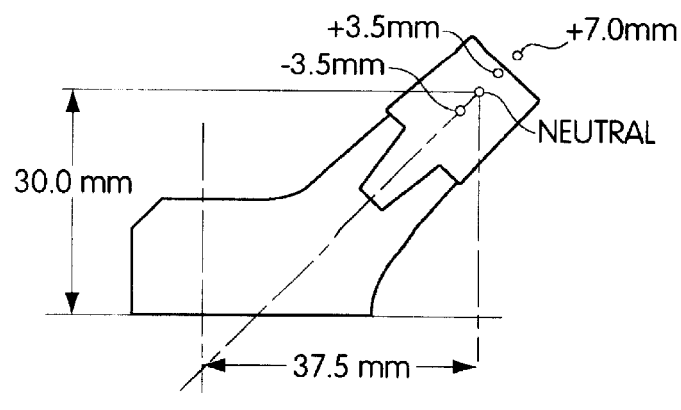
Figure 6E:
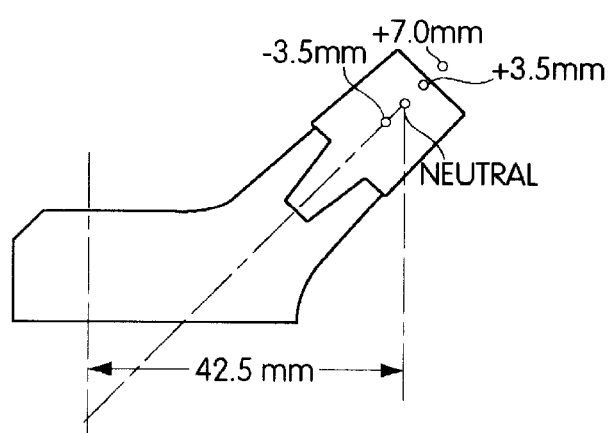
Figure 6F:
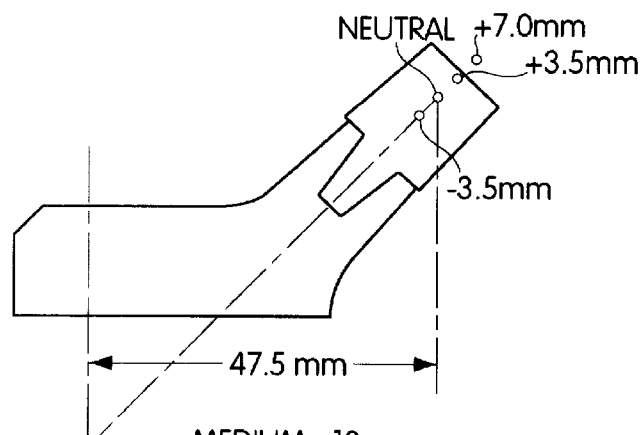
Figure 6G:
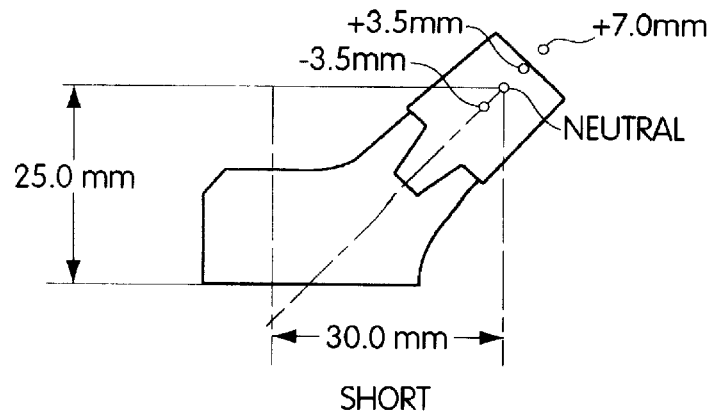
Figure 6H:
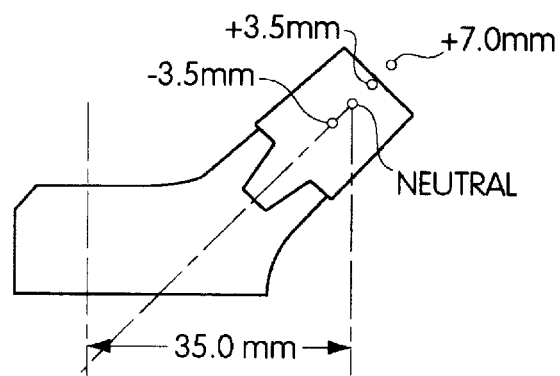
Figure 6I:
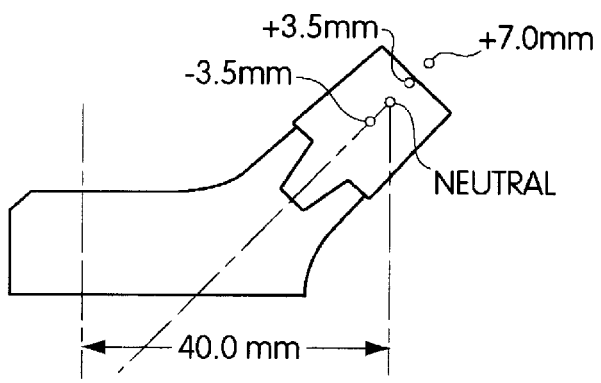

In addition, optimal positioning (including lateral offset and leg length) may be achieved by choosing the appropriate neck portion to use with the chosen stem portion, as shown by the graph in FIG. 5. For instance, for a given stem, a combination of 9 available neck sizes coupled with 4 modular heads with varying offsets, gives the surgeon the choice of 36 lateral offset/leg length positions. In addition, each of these 36 positions can be further adjusted by rotation of the neck portion independent of the stem portion prior to final seating of the neck portion, resulting an optimal combination of anteversion, lateral offset, and leg length. While the data in FIG. 5 were produced using a constant neck angle of 135 degrees for the 9 neck sizes, varying neck angles could be employed across the different neck sizes or as additional options for each neck size. FIG. 6 illustrates a range of various neck sizes used to produce the data shown on the graph of FIG. 5. The silhouettes 6A–6I shown in FIG. 6 provide for long (6A–C), medium (6D–6F) and short (6G–6I) necks. The long neck silhouette may have a height of 35 mm; the medium neck silhouette may have a height of 30 mm; the short neck silhouette may have a height of 25 mm. This height is shown as a y-coordinate on the graph of FIG. 5, and as a vertical measurement on the silhouettes of FIG. 6. The amount of lateral offset may vary for each short, medium or long neck silhouette. The lateral offset is shown as the x-coordinate on the graph of FIG. 5, and as a horizontal measurement on the silhouettes of FIG. 6. The silhouettes shown in FIG. 6 illustrate the versatility of the systems and methods of the present invention, allowing the surgeon to select the component best suited for the particular patient. It is understood that other combinations of neck size and shape, vertical height and lateral offset may be arranged to adapt the present invention to patient requirements.

Figure 7:
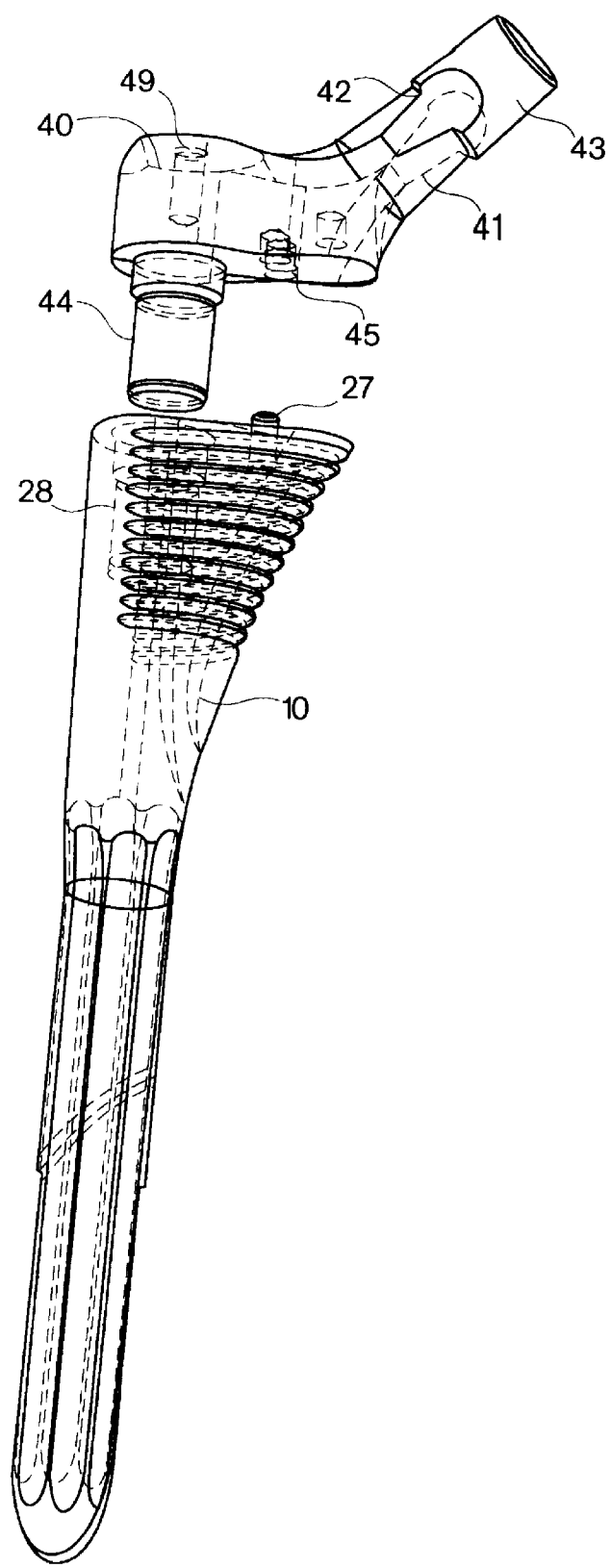
FIG. 7 is an exploded transparent view of the modular stem and neck portions and locking/positioning geometry of an embodiment of the present invention.

While a minimum of two to as large as twelve discrete positions are obtainable, it is preferred to have three to six discrete positions of the neck portion (40). As shown in FIG. 7, primary positioning may be obtained by indexing the keyed portion (27) of the stem (10) to that of the receiving slot (45) of the neck (40). Final locking may be obtained by the male cylindrical spigot (44) of the neck portion (40) locking within the corresponding cylindrical bore (28) of the stem portion (10). This locking may be achieved by one or more zones of diametrical interference between the spigot and bore. The diametrical interference between the cylindrical spigot and the bore is critical to proper functioning of the device, and may be in the range of 0.0005" to 0.0030". In one embodiment, there may be a nominal diametrical interference of 0.0020" at the proximal end of the spigot and bore and a nominal diametrical interference of 0.00010" at the distal end of the spigot and bore. The zone of diametrical interference may be limited to a proximal band (46) of approximately 0.040" to provide increased rotational resistance of the neck within the stem means, while maintaining reasonable assembly forces by controlling the amount of interference, the length of the zone and the axial location of the zone. In one embodiment, both the spigot and bore may incorporate gradual tapers and/or rounds at the surfaces leading into the zones of diametrical interference so as to avoid plowing of one or more surfaces during assembly and thus ease assembly of the neck portion to the stem portion. The length of the cylindrical spigot (44) is not critical; it only requires a length adequate to ensure a suitable locking surface and adequate axial engagement. It has been determined that a length of approximately 0.8" is satisfactory, although lengths selected from a range extending from 0.25" to 2.0" may offer advantages. In an alternate embodiment, the bore (28) may have a diameter at the base of the bore smaller than the diameter at the corresponding portion of the pigot, which allows for increased resistance to axial distraction of the neck portion from the stem portion. This difference in diameter is in the range of 0 to 0.020", and may be achieved in a multitude of ways, including continuous straight or curved surfaces, or discontinuous (stepped) surfaces.

FIG. 7, like FIG. 3B, depicts a neck wherein the male spigot (44) is formed solid, without a split. In this figure, a proximal bore (49) may be seen in the proximal part of the neck axially aligned with the male spigot. This proximal bore (49) permits the insertion of a tool into the proximal aspect of the neck portion (40) to permit its removal if such removal is required by the patient's condition. The proximal bore (49) may be threaded internally to mate with a threaded tool that can then be used to extract the neck portion (40). Other arrangements for removal tools and appropriately configured proximal bores (49) may be readily envisioned by those of skill in the art.

Figure 8:
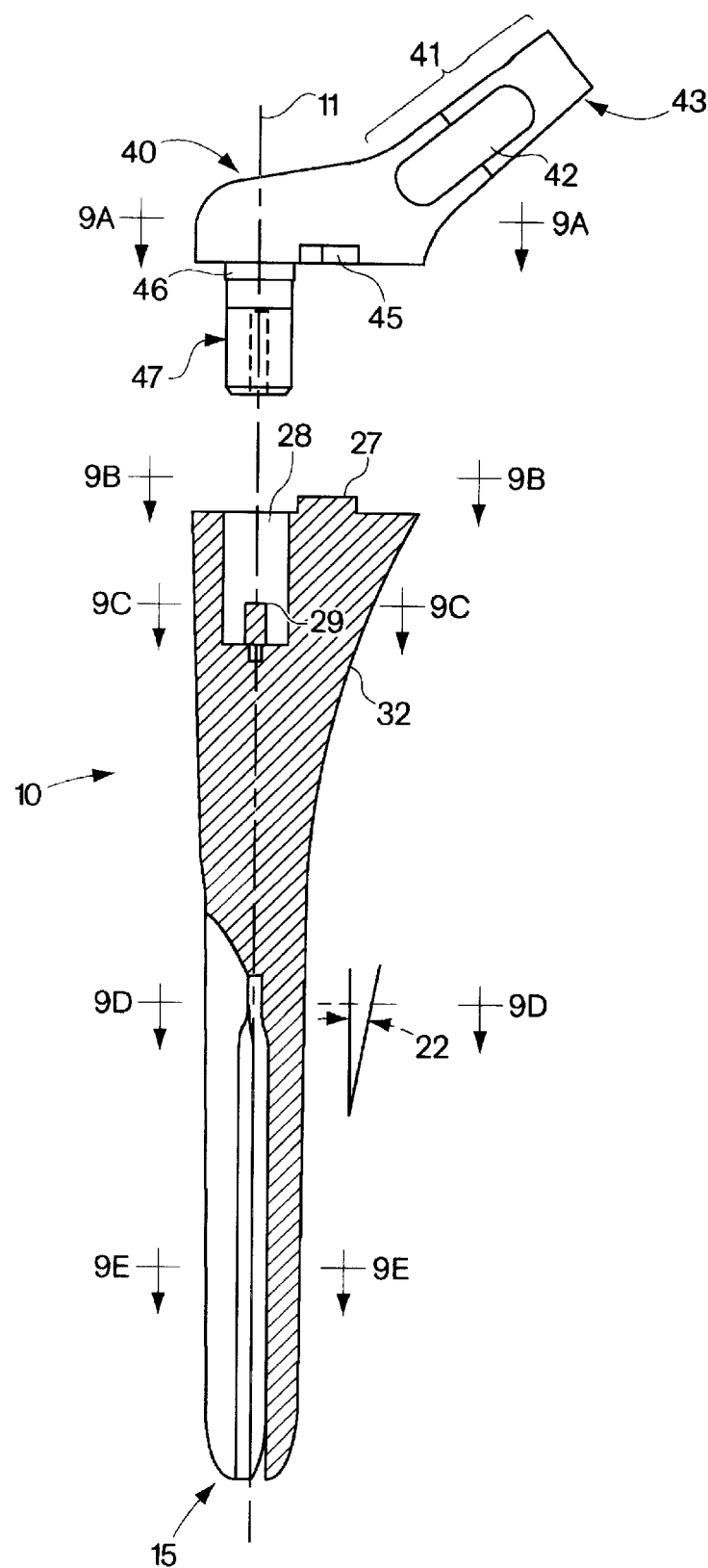
FIG. 8 shows a lateral view of the neck component and a longitudinal cross-section of the stem component of an embodiment of the present invention.

The embodiment of the neck portion (40) shown in FIG. 8 features a male spigot (48) that is split with a single axially directed slot, which may be sagittally oriented as illustrated or oriented in any other biomechanically appropriate plane. A split cylindrical spigot (44) when fully seated may interact with a protrusion (29) located at the base of the cylindrical bore (28). While a minimum of one split, approximately 0.01 inches in width in the cylindrical spigot may be advantageous for locking purposes, more splits of similar or larger dimensions may be incorporated to distribute the locking more equally around the circumference of the bore. In the depicted embodiment, the protrusion (29) becomes inserted into the spigot slot (47) as the neck portion is seated, causing the split spigot (44) to splay outward against the sides of the bore of the stem and thus lock the neck portion (40) to the stem portion (10) and allowing adequate locking and retention of the neck portion (40) to that of the stem (10). The protrusion (29) may act as a wedge forcing the split portions outward. This protrusion (29) can be fabricated by inserting a pin or other suitable member at the base of the bore or may be machined directly. The protrusion (29) can be tapered or cylindrical. Other means of manufacturing of this feature are available to create the protrusion geometry. Optionally, the protrusion (29) can include means whereby a tool can be attached to it for use in removing the stem portion (10) if the clinical situation condition warrants it. One sort of removal means incorporated in the protrusion (29) may include a threaded cavity positioned axially within the protrusion (29), whereby a threaded tool can be matingly inserted into the threaded cavity and used for removing the stem. Other removal arrangements may be envisioned as well that would permit a tool to be used for stem removal. For example, a threaded cylinder could be drilled distally in the central portion of the base of the bore (28), either surrounding a protrusion (29) for a split spigot or in the protrusion's place for a solid spigot. This threaded cylinder could permit the introduction and mating of a threaded tool that could then be used to extract the stem portion from the medullary cavity.

The modular neck portion (40) of the present invention also allows one to utilize different neck configurations with the same stem portion (10) allowing for multiple options for each and every stem. Variations of neck portions (40) can include, both different angled neck portions and neck lengths alone or in combination with each other to achieve varying head positioning, as shown in FIG. 7. Furthermore, as FIGS. 1A and 1B illustrate, when modular heads (30) are attached to these varying neck portions (40) the design options multiply significantly with very little increase in number of individual sub-components such as modular heads and neck portions. The neck (41) of the neck portion (40) is attached to the neck base from which the neck (41) projects outward usually at an angle of 40 to 50 degrees from vertical, preferably 45 degrees. The cross section geometry of the neck projection is generally cylindrical. Neck flats (42), as shown in FIG. 4, may be incorporated in the neck portion (40) to maximize the range of motion of the joint before impingement of the neck occurs on the surrounding structures. In the embodiment depicted in FIG. 4, one end of the neck (41) is blended into the neck base while the opposite end of the neck (41) forms a conical tapered plug or trunnion (43) adapted for receiving the modular hip heads (30) which have a corresponding tapered bore (31). The modular heads (30) are sized such that they fit into a corresponding cup component, implanted in a standard fashion. Metal or ceramic hip heads commonly used in implantable prostheses can be used with the present invention as long as the heads (30) have a suitable corresponding tapered bore (31) that mates with the conical tapered plug (43) at the end of the neck (41).

Figure 9A:
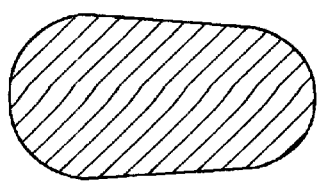
FIG. 9 A–E shows cross-sectional views of the stem portion of the prosthetic device of the present invention taken along the lines 9A—9A, 9B—9B, 9C—9C, 9D—9D and 9E—9E respectively in FIG. 8.
Figure 9B:
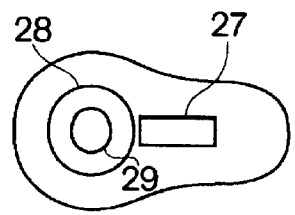
Figure 9C:
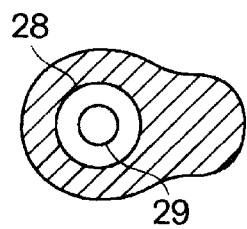
Figure 9D:
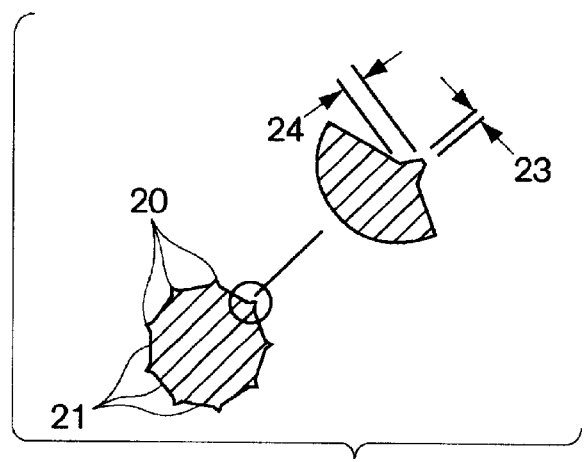
Figure 9E:
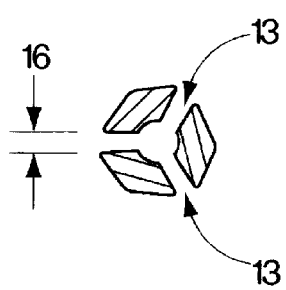

FIGS. 8 and 9A–E show dimensional features of a prosthesis according to the present invention, with FIGS. 9A–E representing transverse cross-sections of the prosthesis at lines designated on FIG. 8 as lines 9A, 9B, 9C, 9D and 9E. While FIGS. 9A, 9B and 9C show transverse cross-sections that illustrate the shape of the neck portion and its coupling and locking mechanisms with the stem portion FIGS. 9D and 9E illustrate the shape of the stem portion itself and certain of its features.

Figures 10, 10A:
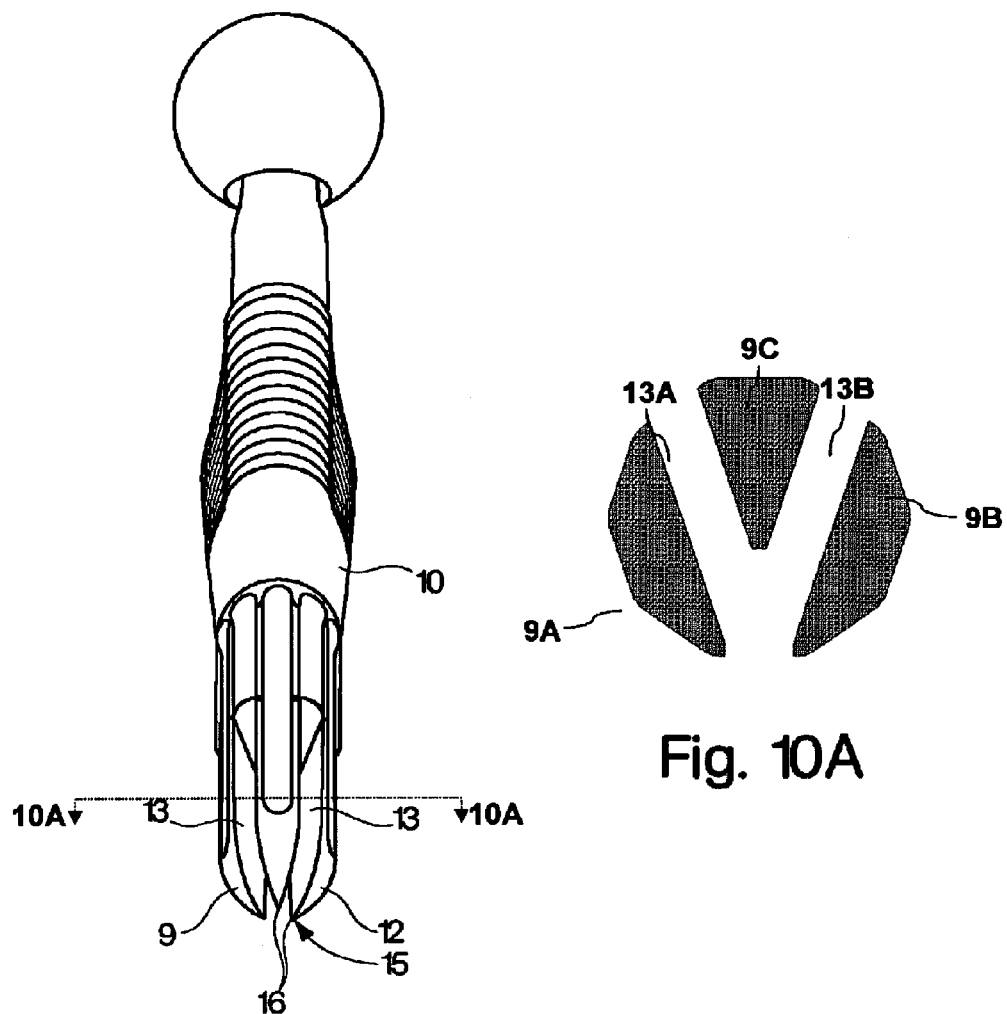
FIG. 10 provides a perspective view of an embodiment of the present invention, showing 2 slots in the distal stem.
FIG. 10A provides a transverse cross-section view taken at line 10A—10A in FIG. 10.
Figure 11:
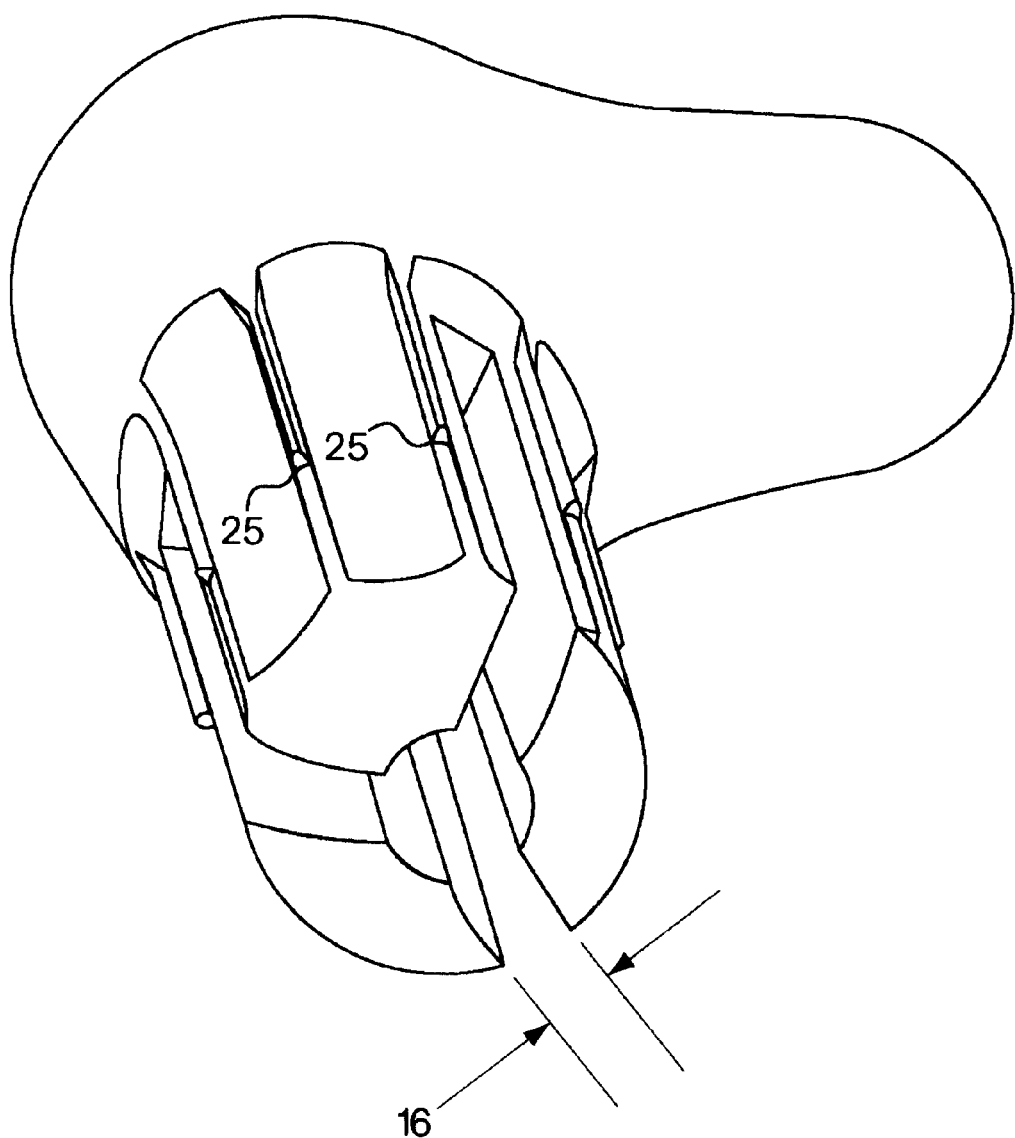
FIG. 11 provides a perspective view of another embodiment of a stem according to the present invention.

FIG. 10 provides a perspective view of a hip prosthesis according to the present invention, highlighting shapes and features of the stem portion (10). The distal stem tip (15) is smooth and may incorporate a spherical or ellipsoidal shape. In certain embodiments, the distal portion (12) of the stem may be slotted resulting in increased flexibility of the stem which minimizes the effects of distal tip impingement of the stem upon the bone and aids in stem insertion. A variety of stem slot configurations may be envisioned. For example, the number of stem slots (13) may vary in proportion to the stem diameter. In the embodiment depicted in FIG. 10, the stem portion (10) has two stem slots (13) that intersect at or near the lateral surface of the stem and are located approximately 36 degrees apart resulting in three elongated portions or tines (9) of the stem connected to each other proximally where the slots terminate and forming the entire stem. The distal tip of each tine (9) may be rounded, angulated or shaped in any pattern that optimizes insertion of the stem into the medullary cavity and that enhances its secure fixation therein. The distal edges of one or more than one tine (9) may be rounded or flattened where a tine edge meets other tine edges. This configuration of stem slots may be suitable for a stem of larger diameter. Intermediate diameter stems may have a single coronal slot resulting in the stem being divided into generally anterior and posterior portions of the stem connected to each other where the slot terminates. The smallest diameter stems may have no stem slot, while the largest diameter stems may have three stem slots. In one embodiment, these slots may be located approximately 120 degrees apart resulting in three elongated portions of the stem connected to each other where the slot terminates and forming the entire stem as shown in FIG. 8 and 9E and in FIG. 11.

FIG. 10A shows a transverse cross-sectional view of the embodiment of FIG. 10 taken at cut line 10A—10A and illustrates the "V slot" tine configuration described above. Two slots (13A) and (13B) are arranged so that they form an acute angle. The slots define three tines (9A), (9B), and (9C). When the stem is implanted in a femur, tine (9C) is oriented so that it is nearer the patient's midline than the other tines and is consequently called the medial tine. Tines (9A) and (9B) are further away from the midline and called lateral tines. When the stem is implanted in a right femur, tine (9A) is called the anterolateral tine, and tine (9B) is called the posterolateral tine, because tine (9A) sits anteriorly (forward) and tine (9B) sits posteriorly (rearward). When the stem is implanted in a left femur, the names are reversed. As shown in FIGS. 10 and 10A, the slots may be oriented longitudinally along the stem and positioned symmetrically, relative to a plane bisecting the stem longitudinally. In this way, tines (9A) and (9B) are each defined by one slot, and the medial tine is defined by both slots. Also as shown in FIGS. 10 and 10A, slot (13A) may be so positioned that the thinnest dimension of lateral tine (9A) is perpendicular to the plane defined by that slot. The same may be true for slot (13B).

The length of each slot may comprise approximately 25%–50% of the stem length (14) where stem length is measured from the distal tip (15) of the stem to the top proximal flat (33) of the stem for standard sized stems for primary hip replacement. Long stem models used for revision purposes would tend to have a larger ratio of slot length to stem length and would be adjusted appropriately upward. The width of the slot (16) can be as small as 0.050 of an inch to as large as 0.200 of an inch. The length and width of the slots may be specified such that the flexibility of an individual tine, under a posterior-medial directed load applied to the distal tip of the stem portion, is a constant or near constant when normalized to the diameter of the diaphyseal segment of the stem portion. The value of this constant, for stems ranging from 8 to 20 mm in diameter, can be in the range of 2 to 6% (percent diameter displacement when subjected to a posterior-medial distal tip load of 100 N), with a preferred value of approximately 4%. Stem diameters for this hip prosthesis range in size from 8 to 20 mm and would be suitable for most of the population. Patients requiring sizes smaller or larger, although uncommon, are accommodated through custom/patient specific devices.

Figure 12:
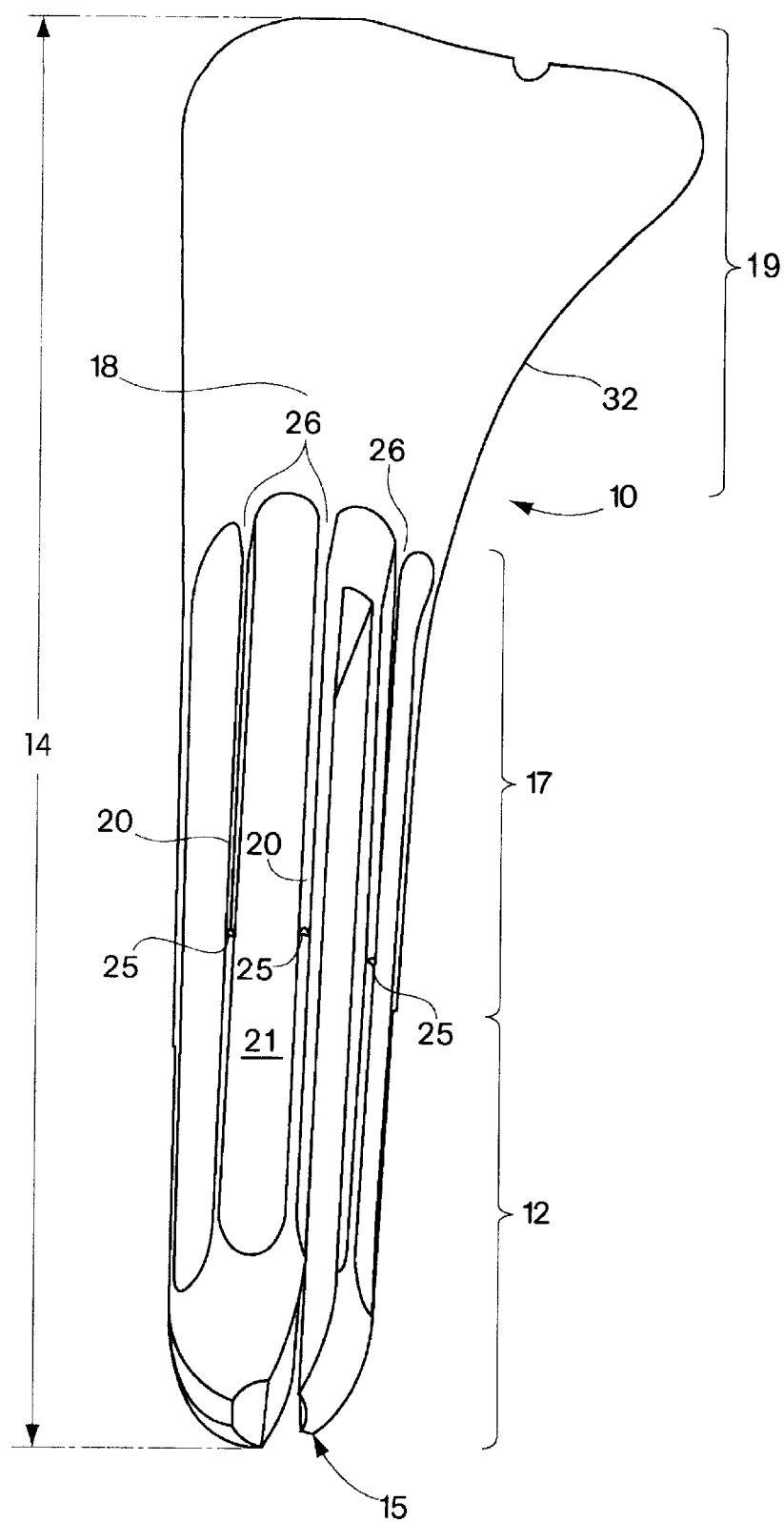
FIG. 12 presents an anterior perspective view of yet another embodiment of a stem according to the present invention.

FIG. 12 shows that the mid-shaft portion (17) of the stem portion (10) incorporates ridges (20) while the distal portion (12) of the stem is free of any hindrance to rotation of the device within the medullary canal. Both the mid shaft (17) and distal portion (12) of the stem are generally either cylindrical or conical in shape or a combination of both. The mid shaft portion may include longitudinal ridges with intervening flutes to aid in positioning of the stem and to provide increased rotational stability of the stem in the bone. The mid shaft portion blends into the relatively larger proximal portion (19) of the stem which is designed to fill the larger bone canal proximally and tends to follow the bone contour of the canal being larger on the medial side (32) of the device.

The flutes (21) may be formed by removing a minimal amount of material from the outer surface of the stem. The slots or land between the ridges (20) around the circumference of the stem become the flutes (21). The ridges (20) are blended into the larger diameter of the stem above while the flutes (21) between the ridges blend into the stem both above and below resulting in a smooth transition of the stem surface, separated by the longitudinal ridges (20) which are equally spaced around the circumference of the stem in the mid-shaft. The ridges (20) cross-sectional shape is generally trapezoidal with the ridge thickness (23) being measured at the top or prominent surface of the ridge, seen also in FIG. 9D.

The mid shaft portion taper angle (22) can be adjusted from no taper (cylindrical) as shown in FIG. 8 to taper angles up to 45 degrees. Preferably this taper angle (22) is in the range of zero degrees to five degrees. Spacing of the ridges can be adjusted to maximize or minimize amount of bone purchase desired and is determined by the number of ridges (20), the thickness (23) of the ridges (20) and the mid-shaft stem diameter. The number of ridges (20) can range from a minimum of one to a number sufficient to allow for adequate fixation of the stem within the canal being limited only by the thickness (23) of the ridge and diameter of the stem. The number of ridges (20) preferably ranges from three to twelve. The thickness (23) of the ridges ranges from 0.002" to 0.050" and is preferably 0.005" to 0.010". Typical stem diameters range from 8 mm to 20 mm and can go beyond this range for special situations.

In one embodiment, the ridges (20) may be parallel to each other and to the long axis of the stem (11) to allow for proper stem insertion. The bone purchase and resulting fixation can also be controlled by the depth (24) of the flutes which can range from 0.25 mm to 2 mm relative from the stem surface (18) and is preferably 0.25 mm to 1 mm. As shown in FIG. 12, leading (25) and trailing (26) portions of the ridges (20) can be, but are not required to be tapered such that both ends terminate in a point and that the mid portion of the ridge (20) is thicker than the leading (25) or trailing (26) portion. The portion between the ridges may be continuous with the stem surface (18) both above and below the mid-shaft portion (17) or may be depressed such that additional material is removed from between the ridges (20) resulting in the stem surface between the ridges (20) being lower than the stem surface (18) above or below the mid-shaft portion (17).

The location of the mid-shaft portion (17) on the stem portion (10) may be varied on different stem components to permit the surgeon greater flexibility in selecting the proper component for the patient's anatomy. The location of the midshaft portion (17) on the stem portion (10) is determined by measuring the distance from the distal tip (15) to the base of the mid-shaft portion (17) and can be expressed as a function of total stem length (14). This distance can be as small as 10% of the stem length (14) to as large as 75% of the stem length (14), and is preferably 20 to 40% of stem length for primary stem designs. Long stem revision models may be adjusted appropriately.

Both the mid shaft (17) and distal portion (12) of the stem are generally either cylindrical or conical in shape or a combination of both. The mid shaft portion then blends into the relatively larger proximal portion (19) of the stem which is designed to fill the larger bone canal proximally and tends to follow the bone contour of the canal being larger on the medial side (32) of the device. In the modular embodiment of the invention, centrally located in the proximal portion of the stem is a cylindrical bore (28) aligned with the longitudinal stem axis (11). Also located on this surface is the key or tab (27).

FIG. 13 presents a perspective view of the stem portion (10) that illustrates the proximal features of this component. The cylindrical bore (28) and its central protrusion (29) identified on this figure have been previously discussed. The angulation key (27) is shown here as a rectangular protrusion, but may be formed in any appropriate shape to secure the neck portion at a preselected angle relative to the coronal plane of the patient. Also apparent in this figure is a proximal flat platform (33) upon which rests the medial body of the neck portion when the stem portion (10) and the neck portion (40) are mated, as shown in FIGS. 3A and 3B. FIG. 4 shows the corresponding flat surface (48) of the neck portion. These mating flat surfaces permit axial loading forces across the prosthesis to be supported uniformly by the widest portion of the prosthetic stem.

Both the stem (10) and neck portions (40) of this device can be fabricated from any suitable high strength biocompatible material. Suitable materials include any of the titanium alloys, Cobalt alloys, or stainless steel alloys. Preferred examples include Ti-6Al-4V and Co—Cr alloys. Embodiments of the present invention may be adapted for use with or without surgical cement or other fixative.

The modular components of a prosthetic device according to the present invention are particularly well-suited for inclusion in a kit that can be used by the surgeon to construct an implant specifically tailored to the patient's anatomy and dimensions. A kit may include a variety of components of different dimensions and shapes, including stem members, neck members and head members, from which the surgeon can select a set of components dimensionally adapted for a particular patient. This allows the surgeon flexibility in assembling a complete prosthesis based on an individual patient's anatomy, either as determined at the time of surgery or as determined in advance.

Figure 14A:
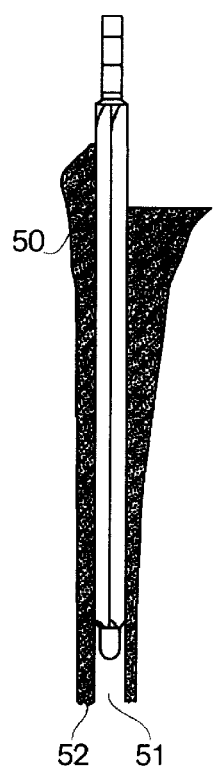
FIG. 14 A–D provides schematic illustrations of steps in a method according to the present invention.
Figure 14B:
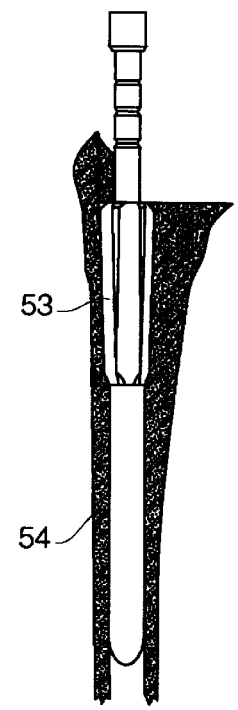
Figure 14C:
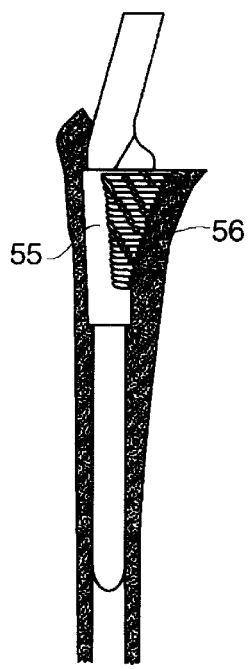
Figure 14D:
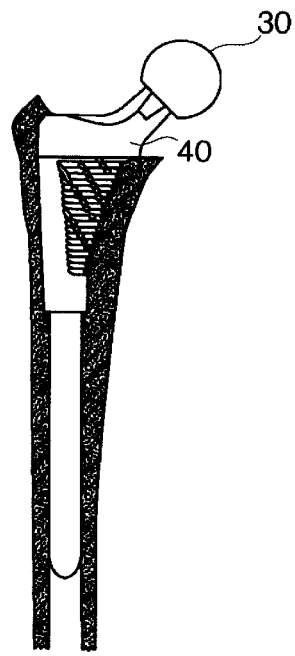

The surgical method for using the joint replacement system of the present invention relates to the particular features of the device itself. In one practice of the methods of the present invention, a surgical technique may be used that includes the following steps, as illustrated in FIG. 14 A–D. The figures do not illustrate the preparation of the joint socket, which may be done in a standard manner. The following steps apply to the methods of the present invention. As shown in FIG. 14A, the proximal joint head is resected and a straight reamer (50) is inserted in the medullary cavity (51) and driven distally to ream out the medullary bone and expose the diaphyseal cortical bone (52). As shown in FIG. 14B, a conical reamer (53) with a pilot shaft (54) matching the distal reamed diameter is used on the proximal end of the bone shaft to create a cavity that approximates the appropriate proximal stem size. As shown in FIG. 14C, when these systems and methods are used for placement of a hip implant, a broach (55) is then used to expand the reamed cavity in the region of the medial calcar (56) of the proximal femur, leaving the conical anteroposterior and lateral surfaces unaffected. A trial neck and head may be attached to the broach to allow trial reduction of the reconstructed joint and selection of an appropriate size and shape for neck and head components. As shown in FIG. 14D, the broach is removed and the stem (10) is inserted. The stem (10) can be preassembled with other components, e.g., on a back table in the O.R., or the stem (10) can be inserted first and then fitted with an appropriately dimensioned neck (40) and head (30). This latter option allows for trialing a head (30) and a neck component (40) separately, without attaching them initially to a stem (10). If the stem (10) is inserted first, the head (30) and neck (40) may be attached to the stem either sequentially or as a unit. Other component systems and other bone preparation tools may be used in other anatomic locations, with the tool and the surgical methods adapted for the size and shape of the long bone and the joint architecture. Measurements for determining appropriate sizes and shapes may be made intraoperatively, preoperatively or both, allowing the surgeon flexibility in selection of size and shape, and further allowing the surgeon to alter the preoperative treatment plan based on intraoperative findings.

While this detailed description has disclosed certain specific embodiments of the present invention for illustrative purposes, various modifications will be apparent to those skilled in the art which do not constitute departures from the spirit and scope of the invention as defined in the following claims.

The invention claimed is:

1. A joint prosthesis, comprising:
   a head member so sized and shaped as to be articulatable with a joint socket, the head member defining a head bore;
   a neck member, having
      a base;
      a plug protruding from the base so sized and shaped as to be receivable in the head bore; and
      a spigot protruding from the base, the spigot having a first cylinder adjacent the base, and a second cylinder having a diameter and being disposed adjacent the first cylinder, the first cylinder having a diameter greater that the diameter of the second cylinder; and
   a stem member, having
      a proximal end defining a stem bore, the stem bore sized and shaped for receiving the spigot and having a first cylindrical portion engaging the periphery of the first cylinder of the spigot by friction-tight press-fit with the first cylindrical portion of the stem bore; and
      a shaft extending from the proximal end and being sized and shaped for seating in a cavity of a long bone.

2. The joint prosthesis of claim 1, wherein the base of the neck member defines at least one receptacle.

3. The joint prosthesis of claim 2, wherein the stem member further comprises a key protruding from the proximal end, the key so positioned as to be received in the at least one receptacle of the neck member as the stem bore receives the spigot.

4. The joint prosthesis of claim 3, wherein the base of the neck member further defines a plurality of receptacles, and the key is selectively positionable in one of the plurality of receptacles.

5. The joint prosthesis of claim 1, wherein the spigot further comprises a transition zone of tapering diameter positioned between the first cylinder and the second cylinder.

6. The joint prosthesis of claim 1, further comprising a protrusion fixedly located in the stem bore, wherein the spigot is distally so split as to define thereby at least one axially oriented slot, and wherein the protrusion is sized, shaped, and positioned for insertion into the axially oriented slot as the spigot is inserted into the stem bore, the protrusion further being sized and shaped for radially expanding the spigot to secure the spigot within the stem bore as the spigot becomes fully seated in the stem bore.

7. The joint prosthesis of claim 1, wherein the stem member further comprises a distal end, the distal end defining at least one axially oriented slot.

8. The joint prosthesis of claim 1, wherein the shaft terminates in a distal end having at least three tines defined by slots in the shaft, the slots forming an acute angle.

9. The joint prosthesis of claim 1, wherein the base of the neck member has a longitudinal axis, and wherein the spigot and the plug protrude from the base in the same plane, the spigot protruding at substantially a right angle to the longitudinal axis of the base, and the plug protruding at an angle of 40 to 50 degrees relative to the longitudinal axis of the base.

10. The joint prosthesis of claim 1, wherein the bore defines a second cylindrical portion for engaging the periphery of the second cylinder of the spigot by friction-tight press-fit when the stem bore receives the spigot.

11. A joint prosthesis, comprising:
    a head member so sized and shaped as to be articulatable with a joint socket, the head member defining a head bore;
    a neck member, having
       a base;
       a plug protruding from the base so sized and shaped as to be receivable in the head bore; and
       a spigot protruding from the base and including a locking band with a constant cross-sectional geometry along its length; and
    a stem member, having
       a proximal end defining a stem bore, the stem bore sized and shaped for receiving the spigot, the bore having a receiving portion with a constant cross-sectional geometry, the receiving portion engaging the locking band of the spigot in the stem bore by friction-tight press-fit, with the neck member fully seated on the stem member; and
       a shaft extending from the proximal end and being sized and shaped for seating in a cavity of a long bone.

12. The joint prosthesis of claim 11, wherein the locking band and the receiving portion are substantially cylindrical.

13. The joint prosthesis of claim 11, wherein the spigot has a free end that terminates with a taper.

14. The joint prosthesis of claim 11, wherein the base of the neck member defines at least one receptacle.

15. The joint prosthesis of claim 14, wherein the stem member further comprises a key protruding from the proximal end, the key so positioned as to be received in the at least one receptacle of the neck member as the stem bore receives the spigot.

16. The joint prosthesis of claim 15, wherein the base of the neck member further defines a plurality of receptacles, and the key is selectively positionable in one of the plurality of receptacles.

17. The joint prosthesis of claim 11, wherein the shaft terminates in a distal end having at least three tines defined by slots in the shaft, the slots forming an acute angle.

18. The stem component of claim 17, wherein at least one of the tines has at least one sharp cutting edge.

19. The stem component of claim 17, wherein the distal end has three tines defined by two slots.

20. The stem component of claim 19, wherein the two slots are oriented longitudinally along the stem and symmetrically, relative to a plane bisecting the stem longitudinally, so that an anterolateral tine is defined by one slot, a posterolateral tine is defined by the other slot, and a medial tine is defined by both slots.

21. The stem component of claim 19, wherein the two slots intersect at or adjacent the lateral surface of the stem.

22. The stem component of claim 17, wherein each slot is cut completely across the stem cross section.

* * * * *

UNITED STATES PATENT AND TRADEMARK OFFICE
CERTIFICATE OF CORRECTION

PATENT NO. : 7,044,975 B2 Page 1 of 1
APPLICATION NO. : 10/605322
DATED : May 16, 2006
INVENTOR(S) : Cheal et al.

It is certified that error appears in the above-identified patent and that said Letters Patent is hereby corrected as shown below:

Column 12,
Line 10, replace "0.00010" with --0.0010--.
Line 30, replace "pigot" with --spigot--.

Column 19,
Line 8, replace "stem component" with --joint prosthesis--.
Line 10, replace "stem component" with --joint prosthesis--.

Column 20,
Line 1, replace "stem component" with --joint prosthesis--.
Line 7, replace "stem component" with --joint prosthesis--.
Line 9, replace "stem component" with --joint prosthesis--.

Signed and Sealed this

First Day of August, 2006

JON W. DUDAS
*Director of the United States Patent and Trademark Office*